US011883557B2

(12) United States Patent
Reed et al.

(10) Patent No.: US 11,883,557 B2
(45) Date of Patent: *Jan. 30, 2024

(54) TUNABLE, CONTROLLED-RELEASE, URETHANE-CONTAINING ELASTOMERS AND PROCESSES OF FORMING THE SAME

(71) Applicant: THE SECANT GROUP, LLC, Telford, PA (US)

(72) Inventors: Stephanie Reed, Conshohocken, PA (US); Carissa Smoot, Harleysville, PA (US); Dennis Shull, Phoenixville, PA (US); Todd Crumbling, Perkasie, PA (US); John D'Ottavio, Telford, PA (US); Peter D. Gabriele, Frisco, TX (US); Jeremy J. Harris, Doylestown, PA (US); Charles Brendan Nicholson, Coopersburg, PA (US); Jared Ely, Quakertown, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/662,462

(22) Filed: May 9, 2022

(65) Prior Publication Data
US 2022/0257828 A1 Aug. 18, 2022

Related U.S. Application Data

(63) Continuation of application No. 17/148,130, filed on Jan. 13, 2021, now Pat. No. 11,406,732, which is a continuation of application No. 16/547,175, filed on Aug. 21, 2019, now Pat. No. 10,918,764.

(60) Provisional application No. 62/872,793, filed on Jul. 11, 2019, provisional application No. 62/720,412, filed on Aug. 21, 2018.

(51) Int. Cl.
| | |
|---|---|
| *A61L 27/18* | (2006.01) |
| *A61L 27/54* | (2006.01) |
| *A61K 31/522* | (2006.01) |
| *B29C 67/24* | (2006.01) |
| *B33Y 80/00* | (2015.01) |
| *B33Y 10/00* | (2015.01) |
| *B29C 64/10* | (2017.01) |

(52) U.S. Cl.
CPC ............ *A61L 27/18* (2013.01); *A61K 31/522* (2013.01); *A61L 27/54* (2013.01); *B29C 67/246* (2013.01); *B33Y 80/00* (2014.12); *B29C 64/10* (2017.08); *B33Y 10/00* (2014.12)

(58) Field of Classification Search
None
See application file for complete search history.

(56) References Cited

U.S. PATENT DOCUMENTS

| | | | |
|---|---|---|---|
| 6,500,239 B2 | 12/2002 | Castellano et al. | |
| 9,731,051 B2 | 8/2017 | Pinchuk et al. | |
| 10,918,764 B2* | 2/2021 | Reed | A61K 9/2031 |
| 11,406,732 B2* | 8/2022 | Reed | A61K 47/34 |
| 2003/0118692 A1 | 6/2003 | Wang et al. | |
| 2008/0033086 A1 | 2/2008 | Jimenez et al. | |
| 2009/0047256 A1 | 2/2009 | Bettinger et al. | |
| 2009/0093565 A1 | 4/2009 | Yang et al. | |
| 2009/0208540 A1 | 8/2009 | Kuzma et al. | |
| 2013/0231412 A1 | 9/2013 | Langer et al. | |
| 2015/0344618 A1 | 12/2015 | Nicholson et al. | |
| 2017/0246316 A1 | 8/2017 | Wroblesky et al. | |

FOREIGN PATENT DOCUMENTS

CN 101597470 B 5/2012

OTHER PUBLICATIONS

Pereira et al. (A highly Tunable Biocompatible and Multifunctional Biodegradable Elastomer, Adv Mater 2013, 25; p. 1209-1215) (Year: 2013).*
Barrett et al., "Extended Duration MK-8591-Eluting Implant as a Candidate for HIV Treatment and Prevention", Antimicrob. Agents Chemother., vol. 62, Issue 10, e01058-18 (13 pages), 2018.
Frydrych et al., "Thermoresponsive, stretchable, biodegradable and biocompatible poly(glycerol sebacate)-based polyurethane hydrogels", Polymer Chemistry, vol. 6, pp. 7974-7987, 2015.
Frydrych et al., "Fabrication, structure and properties of three-dimensional biodegradable poly(glycerol sebacate urethane) scaffolds", Polymer, vol. 122, pp. 159-168, 2017.
Pereira et al., "A Highly Tunable Biocompatible and Multifunctional Biodegradable Elastomer", Adv. Mater., vol. 25, pp. 1209-1215, 2013.

(Continued)

*Primary Examiner* — Melissa S Mercier
(74) *Attorney, Agent, or Firm* — McNees Wallace & Nurick LLC

(57) ABSTRACT

A process forms an implantable product including poly (glycerol sebacate) urethane (PGSU) loaded with an active pharmaceutical ingredient (API). The process includes homogeneously mixing a flowable poly(glycerol sebacate) (PGS) resin with the API and a catalyst to form a resin blend. The process also includes homogeneously combining the resin blend with an isocyanate to form a reaction mixture and injecting the reaction mixture to form the PGSU loaded with the API. An implantable product includes a PGSU loaded with an API. In some embodiments, the implantable product includes at least 40% w/w of the API, and the implantable product releases the API by surface degradation of the PGSU at a predetermined release rate for at least three months under physiological conditions. In some embodiments, the PGSU is formed from a PGS reacted with an isocyanate at an isocyanate-to-hydroxyl stoichiometric (crosslinking) ratio in the range of 1:0.25 to 1:1.25.

32 Claims, 18 Drawing Sheets

(56) References Cited

OTHER PUBLICATIONS

Rogers, "Everything you need to know about injection molding", available at https://www.creativemechanisms.com/blog/everything-you-need-to-know-about-injection-molding, dated Dec. 21, 2015.

Zhang et al., "High Shear Mixers: A review of typical applications and studies on power draw, flow pattern, energy dissipation and transfer properties", Chemical Engineering and Processing, vol. 57-58, pp. 25-41, (2012).

\* cited by examiner

FIG. 29A
FIG. 29B
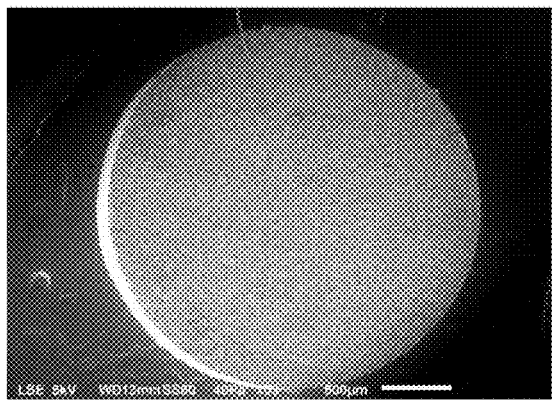
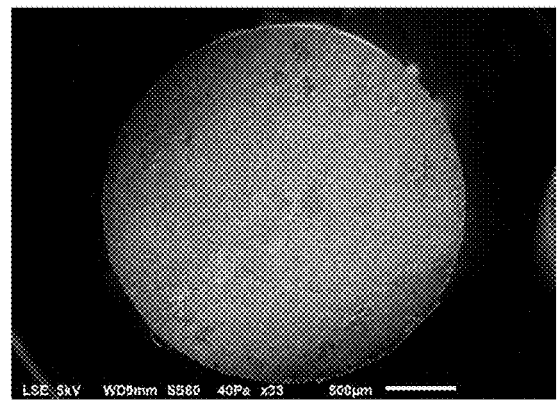
FIG. 30
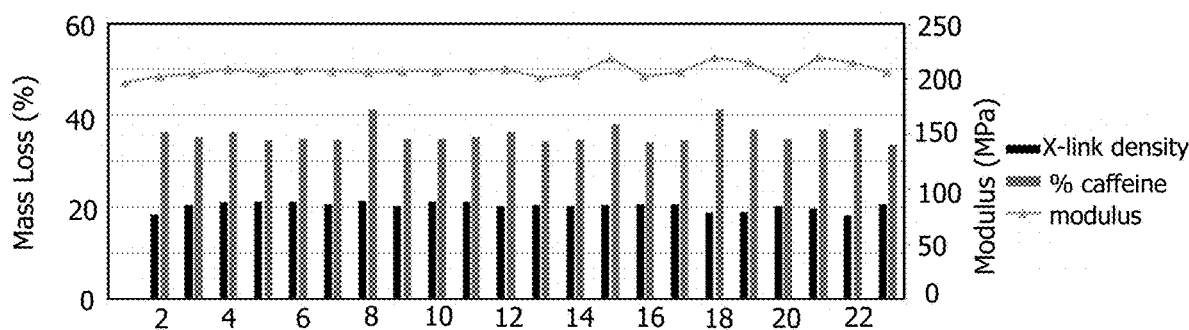
FIG. 31
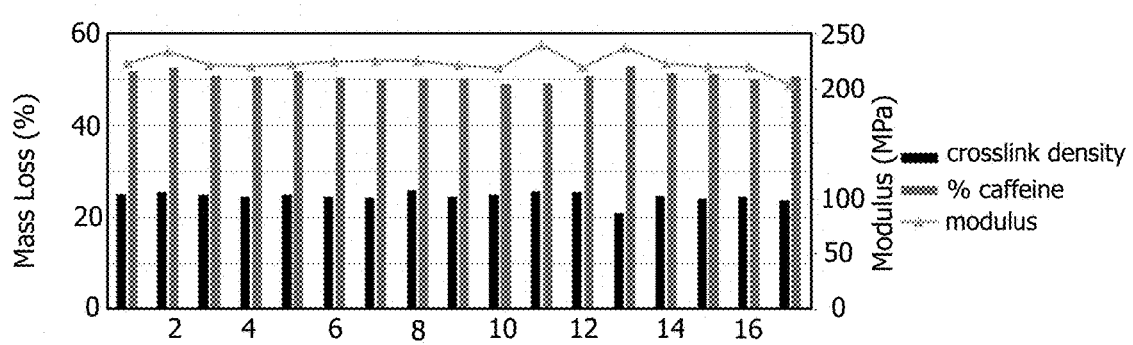

TUNABLE, CONTROLLED-RELEASE, URETHANE-CONTAINING ELASTOMERS AND PROCESSES OF FORMING THE SAME

CROSS-REFERENCE TO RELATED APPLICATIONS

This application is a continuation of co-pending U.S. patent application Ser. No. 17/148,130, filed Jan. 13, 2021, which is a continuation of U.S. patent application Ser. No. 16/547,175, filed Aug. 21, 2019 and issued on Feb. 16, 2021 as U.S. Pat. No. 10,918,764, which claims priority to and the benefit of U.S. Provisional Application No. 62/720,412 filed Aug. 21, 2018 and U.S. Provisional Application No. 62/872,793 filed Jul. 11, 2019, all of which are hereby incorporated by reference in their entirety.

FIELD OF THE INVENTION

This application is directed to processes of forming urethane-containing polymers and polymers formed by such processes. More specifically, this application is directed to processes of forming poly(glycerol sebacate) urethane polymers with tunable controlled release rates and polymers formed by such processes.

BACKGROUND OF THE INVENTION

The majority of biodegradable biomaterial polymers used for drug delivery are bulk eroders that exhibit a dose-dependent active pharmaceutical ingredient (API) release rate, where increasing the drug loading concentration increases the relative release rate. With such polymers, achieving high drug loadings that also sustain release for greater than 3 months is challenging, because the increased loading also generates a steeper concentration gradient between the polymer matrix and the surrounding environment. That, in turn, drives release to occur faster. Hence, for bulk eroders such as poly(lactic-co-glycolic acid) (PLGA), polyglycolic acid (PGA), polylactic acid (PLA), polycaprolactone (PCL), and others, the release rate is often sufficiently low to achieve greater than three months of controlled release therapy when the loading is about 40% w/w or less, but loadings of about 50% w/w or greater often exhibit significantly faster release rates and thus often only provide at most one month of controlled release therapy.

This same limitation occurs with non-degradable polymers, such as poly(ethylene-co-vinyl acetate) (EVA), polyurethane (PU), and silicone, since bulk eroding and non-eroding drug delivery systems are both diffusion-driven. This is demonstrated, for example, in Barrett et al. ("Extended Duration MK-8591-Eluting Implant as a Candidate for HIV Treatment and Prevention", Antimicrob. Agents Chemother., Vol. 62, Issue 10, 2018), where EVA, PCL, and PLA show a steep increase in release rate as the drug loading increases from 40% w/w, to 50% w/w, to 60% w/w, and to 80% w/w. At 60% w/w loading, release from all three polymers is only 2 months in duration. At 80% w/w, release duration drops to 1 month in duration. Moreover, bulk eroding polymers often demonstrate dose dumping once a critical mass loss has been reached.

While release rate is highly dependent on the solubility of the API, it would be highly advantageous to have a polymer carrier that is capable of delivering APIs across a solubility spectrum in a sustained manner, for at least three months and potentially many months longer. Highly soluble APIs pose a challenge to non-degradable and bulk eroding polymers, since Biopharmaceutical Classification System (BCS) class I (high solubility, high permeability) and class III (high solubility, poor permeability) APIs are likely to rapidly diffuse away from the polymer matrix, causing a large burst release and fast release rate. On the other hand, poorly soluble APIs also pose a challenge to non-degradable and bulk eroding polymers, since BCS class II (low solubility, high permeability) and BCS class IV (low solubility, low permeability) APIs have a difficult time diffusing away from the polymer matrix. Sufficient release rates cannot be achieved, especially within a reasonable timeframe after implantation. The majority of new drug entities developed by the pharmaceutical industry are BCS class II and IV, and so solubility and permeability concerns are becoming increasingly important to manage for effective controlled drug delivery. However, BCS class I and III APIs are still very much of interest for controlled release as well. Thus having a polymeric delivery system that can deliver both highly-soluble and poorly-soluble APIs in the form of a matrix that is essentially agnostic to the API would be desirable. Further, having a polymeric delivery system that does not solely rely on diffusion, but instead releases the API through surface erosion, either in combination with diffusion or by surface erosion alone, is also highly desirable.

A conventional method of producing PGSU polymeric films is solvent-based, using a 10% w/v PGS solution in dimethylformamide (DMF) heated to 55° C. (131° F.) in the presence of catalyst, adding hexamethylene diisocyanate (HDI) dropwise, and allowing to react for 5 hours prior to casting into molds for solvent evaporation (see, for example, U.S. Patent Application Publication No. 2013/0231412, which is hereby incorporated by reference in its entirety). Such conventional methods may reduce the reaction time and/or temperature by inclusion of a catalyst, such as, for example, stannous octoate, triethylene diamine, bis(dimethylaminoethyl)ether, dimethylethanolamine, dibutyltin dilaurate, or a bismuth-based catalyst. The temperature, the solvent, the dropwise isocyanate addition, and the reaction time limitations of this conventional approach are not amenable to API incorporation or high throughput manufacture of an API-loaded product.

A conventional method of producing PGSU polymeric films is solvent-free, using 100% w/v PGS resin, mixing with a pre-mixture of HDI and catalyst, and spin coating onto modified glass coverslips for 3000 rpm for 3 minutes (see, for example, U.S. Patent Application Publication No. 2013/0231412). Such conventional methods may reduce the reaction time and/or temperature by inclusion of a catalyst, such as, for example, stannous octoate, triethylene diamine, bis(dimethylaminoethyl)ether, dimethylethanolamine, dibutyltin dilaurate, or a bismuth-based catalyst. The unspecified mixing technique and the spin coating limitations of this conventional approach are not amenable to uniform HDI mixing, large volume HDI incorporation, API incorporation, or high throughput manufacture of an API-loaded product. Additionally, the pre-mixture of isocyanate and catalyst may cause isocyanate self-condensation and subsequent dimerization, trimerization, and/or formation of other isocyanate self-reaction products, which may reduce the efficiency of the isocyanate-polyol reaction and result in lower crosslinking than desired. The pre-mixture of isocyanate and catalyst may also introduce moisture that the isocyanate will readily and preferentially react with, causing formation of carbamic acid and amine, and in turn causing formation of urea.

What is needed is a process that avoids the use of high temperatures normally required for PGS crosslinking into a thermoset product, a process that permits higher loadings of at least 10% w/w up to 90% w/w API with controlled release of the API for at least three months, a process that incorporates isocyanate volumes equivalent to isocyanate-to-hydroxyl (NCO:OH) stoichiometric ratios between 1:0.25 and 1:1.25, a process that avoids the use of solvents for API loading, a process that handles the high viscosity of solventless PGS and high API loadings, a process that handles the disparate viscosities of solvent-less API-loaded PGS and isocyanate, a process that prevents air bubble formation, air entrainment, and air entrapment during urethane reaction, a process that uniformly and precisely incorporates and distributes PGS, isocyanate, catalyst, and API into a homogeneous blend, a process that can form the homogeneous blend within the working time of the PGSU reaction without compromising uniformity or precision, and/or an elastomer loaded with up to 90% w/w API that provides controlled release of the API for at least three months.

BRIEF DESCRIPTION OF THE INVENTION

Exemplary embodiments are directed to processes that form poly(glycerol sebacate) urethane (PGSU) having a degradation rate and corresponding API release kinetics that are both tunable by selection of the starting PGS polyol structure and the process conditions to form the API-loaded PGSU.

Exemplary embodiments are directed to PGSU formulations that incorporate high API loading and provide sustained API release, independent of loading concentration, to maintain therapeutic levels over the course of many months.

Exemplary embodiments are directed to manufacturing methods for PGSU that eliminate any use of high temperature or solvent, thereby permitting incorporation of thermolabile and form-sensitive APIs into the PGSU.

According to an exemplary embodiment, a process forms an implantable product comprising poly(glycerol sebacate) urethane loaded with an active pharmaceutical ingredient. The process includes homogeneously mixing a flowable poly(glycerol sebacate) resin with the active pharmaceutical ingredient and a catalyst to form a resin blend. The process also includes selecting an amount of isocyanate such that an isocyanate-to-hydroxyl stoichiometric ratio is in the range of 1:0.25 to 1:1.25. The process further includes homogeneously combining the resin blend with the isocyanate to form a reaction mixture and injecting the reaction mixture to form the poly(glycerol sebacate) urethane loaded with the active pharmaceutical ingredient.

According to another exemplary embodiment, an implantable product includes a poly(glycerol sebacate) urethane loaded with an active pharmaceutical ingredient. The implantable product releases the active pharmaceutical ingredient by surface degradation of the poly(glycerol sebacate) urethane at a predetermined release rate for at least three months under physiological conditions.

According to yet another exemplary embodiment, an implantable product includes a poly(glycerol sebacate) urethane loaded with an active pharmaceutical ingredient. The poly(glycerol sebacate) urethane is formed from a poly(glycerol sebacate) reacted with an isocyanate at an isocyanate-to-hydroxyl stoichiometric ratio is in the range of 1:0.25 to 1:1.25.

Various features and advantages of the present invention will be apparent from the following more detailed description, taken in conjunction with the accompanying drawings which illustrate, by way of example, the principles of the invention.

BRIEF DESCRIPTION OF THE DRAWINGS

FIG. 29A shows the cross-section of 40% w/w caffeine-loaded PGSU rod products fabricated by a solvent-less, dual-barrel syringe process that involves high shear mixing and extrusion into molds, for PGSU made from Regenerez® PGS resin.

FIG. 29B shows the cross-section of 60% w/w caffeine-loaded PGSU rod products fabricated by a solvent-less, dual-barrel syringe process that involves high shear mixing and extrusion into molds, for PGSU made from Regenerez® PGS resin.

FIG. 30 shows crosslink density, loading, and elastic modulus of the 40% w/w caffeine-loaded PGSU rod product of FIG. 29A.

FIG. 31 shows crosslink density, loading, and elastic modulus of the 60% w/w caffeine-loaded PGSU rod product of FIG. 29B.

Wherever possible, the same reference numbers will be used throughout the drawings to represent the same parts.

DETAILED DESCRIPTION OF THE INVENTION

Figure 1:
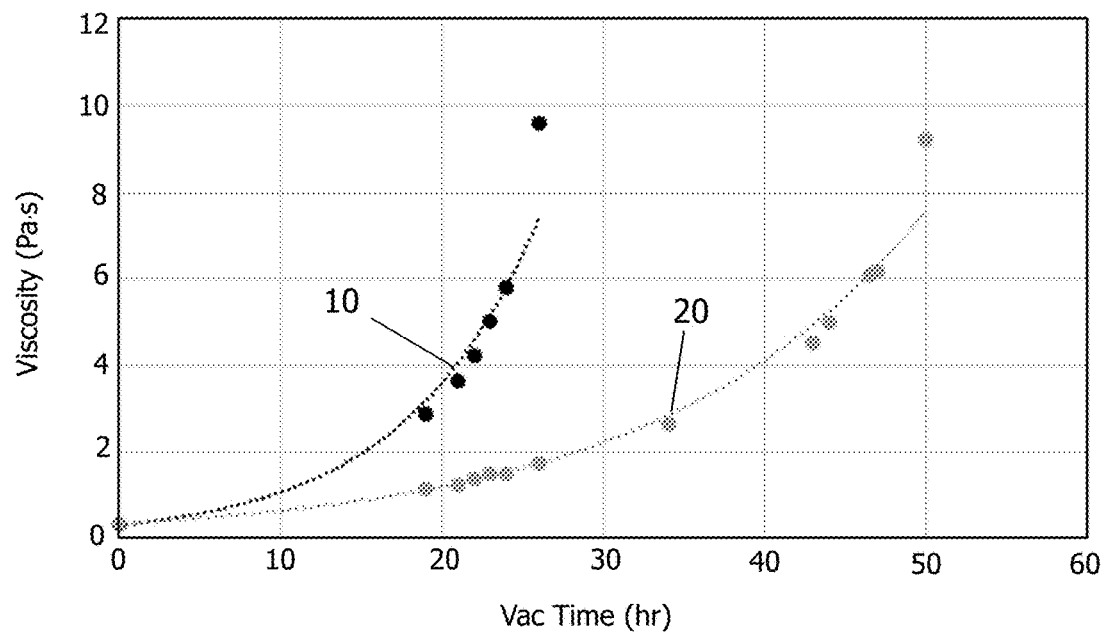
FIG. 1 shows viscosity as a function of reaction time for a water-mediated PGS polymerization process and a non-water-mediated PGS polymerization process.

Provided herein are compositions and processes of forming compositions including poly(glycerol sebacate) urethane (PGSU) polymers with tunable controlled release rates for release of a loaded active pharmaceutical agent (API).

Poly(glycerol sebacate) (PGS) is a cross-linkable elastomer formed as a co-polymer from glycerol and sebacic acid. PGS is biocompatible and biodegradable, reduces inflammation, improves healing, and has antimicrobial properties, all of which make it useful as a biomaterial in the biomedical field.

PGS has limited processability options as a result of the constraints on advancing polycondensation reactions at low temperatures in the presence of an API or active biologic.

Bioresorbable elastomeric urethanes have been developed as a source of engineering material that provides both an elastomeric engineering compliance property to mimic the viscoelastic properties of tissue and a biodegradability property that may be tuned to degrade or deliver in a controlled surface-eroding mechanism, unlike the plastic and rigid lactides and glycolides that bulk degrade and lack sufficient viscoelasticity. Such a surface mechanism makes the polyester polyol, PGS, and its urethane derivative, poly(glycerol sebacate) urethane (PGSU), excellent candidates for controlled drug release. The mechanism of surface erosion for PGS and PGSU is hydrolysis, enzymatic degradation, and oxidative degradation.

As a surface eroder that at least initially shows water impermeability, API-loaded PGSU does not experience a concentration gradient between the internal polymer and external environment, and the release rate is dictated by the rate of surface erosion. Accordingly, PGSU offers a nearly dose-independent API release, where higher drug loading does not dramatically impact the rate of release. PGSU has been shown to maintain a near-constant release rate from 10% w/w to 90% w/w API loadings. Additionally, PGSU has been shown to maintain near zero order release kinetics across 10% w/w to 90% w/w loadings.

PGSU without API loading only swells about 2% w/w over two weeks in saline solution at both 23° C. and 37° C., indicating the low water permeability and hydrophobicity of PGSU as a base material. Unloaded PGSU films with a thickness of 1 mm show no water permeation or percolation over four weeks at 37° C. API-loaded PGSU films with a thickness of 1 mm do experience water permeation and percolation over four weeks at 37° C., but this behavior is dependent on the drug distribution, drug particle size, drug loading, and crosslinking density of the PGSU matrix. If large agglomerations of API are embedded in the PGSU matrix, water or fluids may percolate in, following interconnected channels formed by API particles that are adjacent or touching. Once water percolates in, the water may solubilize and carry away API via diffusion. This can be prevented with thorough mixing of PGSU and the API, potentially by also applying high shear or using grinding media during mixing, to break up agglomerations and/or prevent agglomeration formation. High API loading is another instance where percolation may occur, since the API particles are packed closer together within the matrix. In this case, the homogeneous distribution of API and a small API particle size are critical to preventing interconnected ingress channels from forming. Beyond percolation, water can also permeate into and out of the drug-loaded PGSU matrix. As evidenced by unloaded PGSU films swelling about 2% w/w as mentioned above, this slight amount of liquid transport is enough for water to infiltrate in and help the API diffuse out, but it is dependent on the PGSU wall thickness. This explains why unloaded PGSU films swell slightly but do not demonstrate water penetration through a thickness of 1 mm.

Drug-loaded PGSU films contain much thinner walls of PGSU surrounding API particles, so 2% w/w swelling could allow water to penetrate between regions of API particles. This can be mitigated by increasing the crosslinking density of PGSU, to both slow down the permeation of water through PGSU and also slow down the degradation rate of the thin walls separating API particles. It has been demonstrated that a lower crosslinked PGSU with high drug loading exhibits water percolation and permeation until the water carries the drug through the full 1-mm film thickness. This diffusion is a slow seepage, to the point where the diffused water evaporates on the other side of the film, leaving behind the drug to re-crystallize on the film's back side. In contrast, a higher crosslinked PGSU with the same high drug loading avoids these issues by inhibiting permeation. Higher crosslinked PGSU means a smaller mesh size, which limits permeation. If the mesh size of the polymer is tight enough, small molecules like APIs or even solvents cannot pass through. Percolation and permeation can be related to burst release and diffusion in practice. Reducing percolation and permeation results in reduced burst release and diffusion, so that drug delivery occurs solely by surface erosion and so that diffusion effects are secondary or non-existent.

Urethane chemistry, including that which forms PGSU, is driven by catalytic action. Without precise characterization of the starting polyol, the urethane chemistry to form PGSU does not achieve a reliable urethane-containing elastomer product with predictable crosslinking, degradation rate, and subsequent release kinetics for drug delivery applications. PGS otherwise offers many potential advantages as a starting polyol, namely that it is a surface-eroding elastomer that elicits minimal inflammatory response and degrades into byproducts that are readily metabolized by cells. The high temperatures required to crosslink and thermoset PGS, however, are often a deterrent for API incorporation into a PGS drug delivery device, since many APIs have thermolabile properties.

During API compounding, solvent-free processing eliminates the time and cost associated with drying steps, which may often require an increase in temperature that incurs additional cost. Solvent exposure may also have a detrimental effect on the physical form of the API, causing structural variations that may affect API stability, performance, and efficacy. Heat exposure may similarly have a detrimental effect on API physiochemical characteristics. The absorption, distribution, metabolism, and excretion (ADME) characteristics of an API are typically thoroughly optimized during primary formulation in drug discovery, and any changes to crystallinity, amorphism, polymorphism, salt form, free base form, or free acid form that occur during secondary formulation are undesirable and to be avoided, often at great lengths.

In exemplary embodiments, a manufacturing process reduces or eliminates the use of solvent and heat, thereby creating a manufacturing environment that is suitable for inclusion of thermolabile and form-sensitive APIs, while maintaining rheological properties and a working time suitable for homogeneous mixing followed by rapid part molding. In exemplary embodiments, the manufacturing process is free of solvents and applied heat.

In exemplary embodiments, a manufacturing process is scalable and/or continuous, and reduces or eliminates moisture during homogeneous mixing suitable for high viscosity, disparate viscosity, equivalent volumes, and/or disparate volumes of immiscible components.

In exemplary embodiments, the implantable product is a surface-eroding, flexible PGSU cylindrical rod, formed by reaction injection molding with up to 90% w/w API loading, no solvent use, and no heat exposure above 60° C., that is implantable subcutaneously and sustains zero order or first order release kinetics for up to at least six months.

In exemplary embodiments, the implantable product is formed, in part, from a chemically-characterized poly(glycerol sebacate) (PGS) resin and an isocyanate selected, in part, based on the chemical characterization of the PGS resin. Appropriate isocyanates may be aliphatic or aromatic in structure. Appropriate isocyanates may include, but are not limited to, hexamethylene diisocyanate (HDI), methylene diphenyl diisocyanate (MDI), toluene diisocyanate (TDI), isophorone diisocyanate (IPDI), methylenebis(cyclohexyl isocyanate) (HMDI), tetramethylxylene diisocyanate (TMXDI), aliphatic isocyanates, aromatic isocyanates, aliphatic-aromatic combination isocyanates, and/or blocked isocyanates. Some isocyanates may be slower reacting based on their aliphatic, aromatic, or aliphatic-aromatic combination structure. The speed of reaction may be tuned based on the needs of the manufacturing process of interest.

In some embodiments, the chemically-characterized PGS resin is prepared via a water-mediated polycondensation reaction. The chemically-characterized PGS resin may include a molecular weight above 10,000 Da, alternatively above 15,000 Da, alternatively above 25,000 Da, or any value therebetween. The chemically-characterized PGS resin may include a polydispersity index less than 16, alternatively less than 14, alternatively less than 12, alternatively less than 10, alternatively less than 8, or any value, range, or sub-range therebetween. The chemically-characterized PGS resin may include an acid number between 20 and 80, alternatively between 30 and 70, alternatively between 40 and 60, alternatively between 35 and 55, alternatively between 40 and 50, or any value, range, or sub-range therebetween. The chemically-characterized PGS resin may include a hydroxyl number between 160 and 240, alternatively between 180 and 220, alternatively between 190 and 210, or any value, range, or sub-range therebetween. As used herein, a "hydroxyl number" value is as determined by American Society for Testing and Materials (ASTM) E222. The chemically-characterized PGS resin may include a stoichiometric ratio of glycerol-sebacic acid between 1:0.25 and 1:2, alternatively between 1:0.5 and 1:1.5, alternatively between 1:0.75 and 1:1.25, or any value, range, or sub-range therebetween. The PGSU may be formulated with a stoichiometric ratio of isocyanate-to-hydroxyl between 1:0.25 and 1:2, alternatively between 1:0.25 and 1:1.5, alternatively between 1:0.25 and 1:1.25, or any value, range, or sub-range therebetween. One or more of these parameters may be controlled to tailor the PGSU degradation rate to achieve desired API release kinetics.

In some embodiments, the water-mediated process to form PGS or a similar elastomer follows a procedure disclosed in U.S. Patent Application Publication No. 2015/0344618, which is hereby incorporated by reference in its entirety. It may be desirable to charge the glycerol and water to a vessel in a stoichiometric ratio, water-to-glycerol, of about 1:1 or greater, alternatively about 1:1 to about 4:1, alternatively about 2:1 to about 4:1, alternatively about 2:1 or greater, alternatively about 3:1, or any value, range, or sub-range therebetween. After the glycerol has dissolved in the vessel, sebacic acid is added to the vessel in a predetermined stoichiometric ratio, glycerol-to-sebacic acid, of about 1:0.9 to about 1:2.5, alternatively about 1:1, or any value, range, or sub-range therebetween.

The mixture is then heated to a temperature of about 50° C. to about 200° C. (122° F. to 392° F.), preferably to a temperature of about 140° C. (284° F.) or greater in order to melt the sebacic acid. The mixture is heated for about 1 hour or more and may be stirred while heating. The vessel may be under an inert gas, such as nitrogen or argon, or under a vacuum while it is being heated. After the mixture is heated, it is stirred at an elevated temperature to distribute the contents of the mixture. The stirring step may last up to 1 hour or more. The vessel may be kept under an inert atmosphere while the mixture is being mixed to homogeneity. After the mixture is dispersed, the water is removed by distillation.

In some embodiments, the vessel is heated under nitrogen to about 160° C. (320° F.) for about 1 hour. After the mixture is heated, the mixture is stirred at about 130° C. (266° F.), under nitrogen for about 1 hour to thoroughly disperse the sebacic acid until the mixture is homogeneous. The reaction vessel is then purged with nitrogen for about 24 hours at about 120° C. (248° F.). After the system has been purged, a vacuum of about 10 Torr is applied to the vessel while maintaining a temperature of about 120° C. (248° F.) or higher for about 26 hours.

Distillation may be achieved by heating the mixture, or by putting the vessel under a vacuum, or both. The temperature of the vessel may be about 100 to 200° C. (212 to 392° F.) or preferably about 130 to 150° C. (266 to 302° F.). The pressure of the vessel may be about 760 Torr or lower. In exemplary embodiments, the pressure is 20 Torr or less. The distillation is continued until the polymer reaches a desired average molecular weight, or until no more water is distilled. The removal of water from the vessel allows the monomers to react, thus the polymer has been synthesized by the end of the distillation.

The PGS resin molecular weight, polydispersity index, reaction process, degree of branching, acid number, hydroxyl number, and glycerol-to-sebacic acid stoichiometric ratio all may impact how PGSU is crosslinked and accordingly how PGSU is degraded. Conventional processes do not address any of these parameters for PGSU other than the molecular weight, which is typically restricted to be between 3,000 Da and 25,000 Da. Molecular weights about 25,000 Da or greater offer a slower API release rate that is more suitable for sustained release applications, such as long-acting implantables. It will be appreciated by one of ordinary skill in the art that these parameters may be tailored to fine-tune the API release rate from the biodegradable implantable product. A tight control of these specific parameters to achieve an implantable product with reliable and tunable drug release has not been previously identified. Conventional processes for synthesizing PGS resin without water-mediation during the polycondensation reaction result in a PGS resin with higher polydispersity index for molecular weights greater than 25,000 Da, compared to PGS resin synthesized using water-mediated polycondensation. Conventional processes for synthesizing PGS resin without water-mediation also result in different PGSU crosslinking organization and three-dimensional crosslinking structure than PGS resin synthesized using water-mediated polycondensation, as evidenced by water permeation and percolation testing, even though Flory-Rehner swelling and tensile testing on the bulk material shows a similar crosslinking density and elastic modulus, respectively, and Fourier-transform infrared (FTIR) spectroscopy on the PGS resin material shows similar chemical functionality. Conventional processes for synthesizing PGS resin without water-mediation also result in different amounts and different proportions of extractables than PGS resin synthesized using water-mediated polycondensation. Excess extractables may react with isocyanate, quenching it, resulting in an unintentionally lower crosslinking than expected and/or desired.

In some embodiments, the active pharmaceutical ingredient is incorporated by blending neat API powder with PGS polyol resin prior to urethane reaction. Solvent extraction methods demonstrated no observable cross-reaction of active pharmaceutical ingredient into the polymer network during urethane crosslinking, nor are any detrimental or cross-reaction effects observed after gamma sterilization. The two-component PGSU reaction should be thoroughly mixed within its pot life to achieve API content uniformity and crosslinking uniformity.

Selection of an appropriate isocyanate-to-hydroxyl stoichiometric ratio provides a stable implantable product with optical clarity that does not exhibit clouding, hazing, blooming, or stiffening over time upon storage at room temperature and room humidity ambient conditions. When the isocyanate-to-hydroxyl stoichiometric ratio is less than 1:2, such as, for example, 1:3 or 1:4, the implantable product suffers from clouding and stiffening when stored at ambient conditions, which is detrimental to product shelf life and reflects an unstable product.

Selection of an appropriate isocyanate-to-hydroxyl stoichiometric ratio provides a highly crosslinked implantable product with properties for sustained, surface erosion-mediated drug release for long durations and high drug loadings, namely reduced water percolation and permeation, reduced API burst release and diffusion, and slower PGSU degradation.

Exemplary embodiments formulate PGSU specifically for manufacturing processes, such as molding, particularly without the use of any solvent or heat above 40° C. while still maintaining homogeneous mixing and incorporation of API and isocyanate.

An implantable API-loaded PGSU product may include a PGSU article of manufacture in the form of a monolithic rod, a tube, a film, a sheet, a multi-layered composite, a coating, a fiber, a textile, a porous scaffold, microparticles, and/or nanoparticles. The monolithic rod may have a circular, elliptical, square, or rectangular cross section. The monolithic rod may contain multiple layers or compartments, arranged concentrically, axially, longitudinally, or in another pattern.

Starting polyol characteristics may include a highly-branched PGS prepolymer resin as a starting reactant, a PGS resin with a molecular weight greater than 10,000 Da, a PGS resin with a polydispersity index less than 12, a PGS resin prepared via a water-mediated polycondensation reaction, a PGS resin with an acid number between 30 and 60, a PGS resin with a hydroxyl number between 160 and 240, a PGS resin with a glycerol-to-sebacic acid stoichiometric ratio between 1:0.5 and 1:1.5, or combinations thereof.

Figure 16:
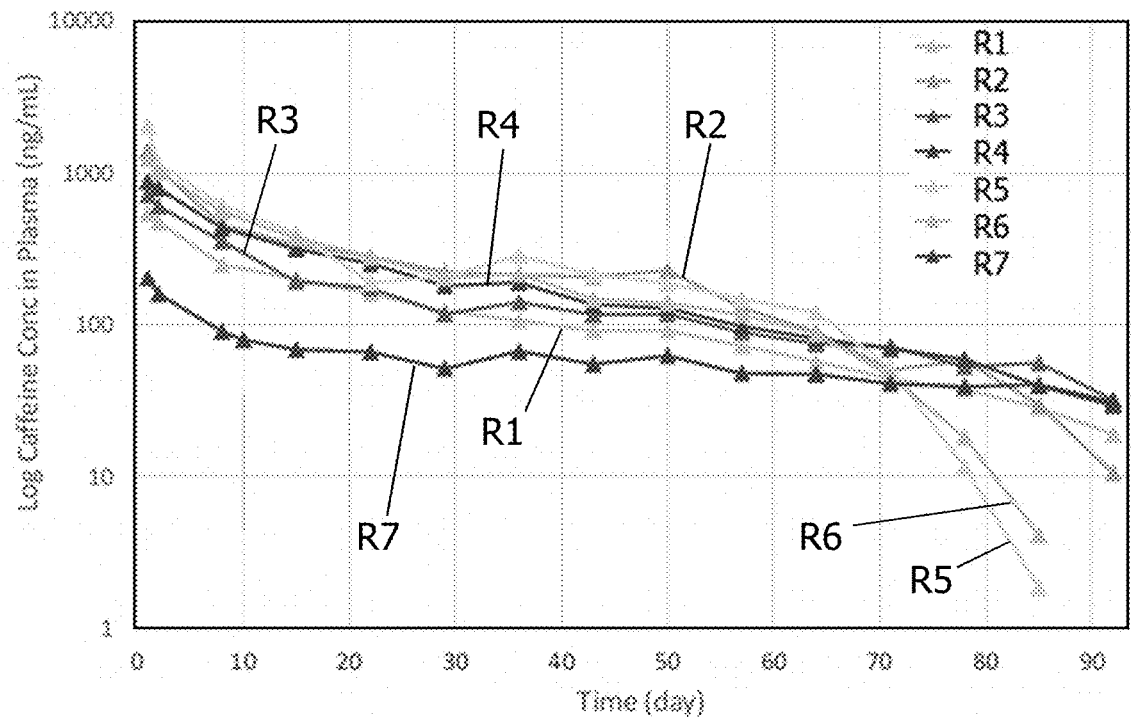
FIG. 16 shows non-cumulative release curves as plasma concentration of API release in vivo for implantable PGSU rod products with 15% to 25% w/w API loadings at different crosslinking densities, for PGSU made from Regenerez® PGS resin.
Figure 17:
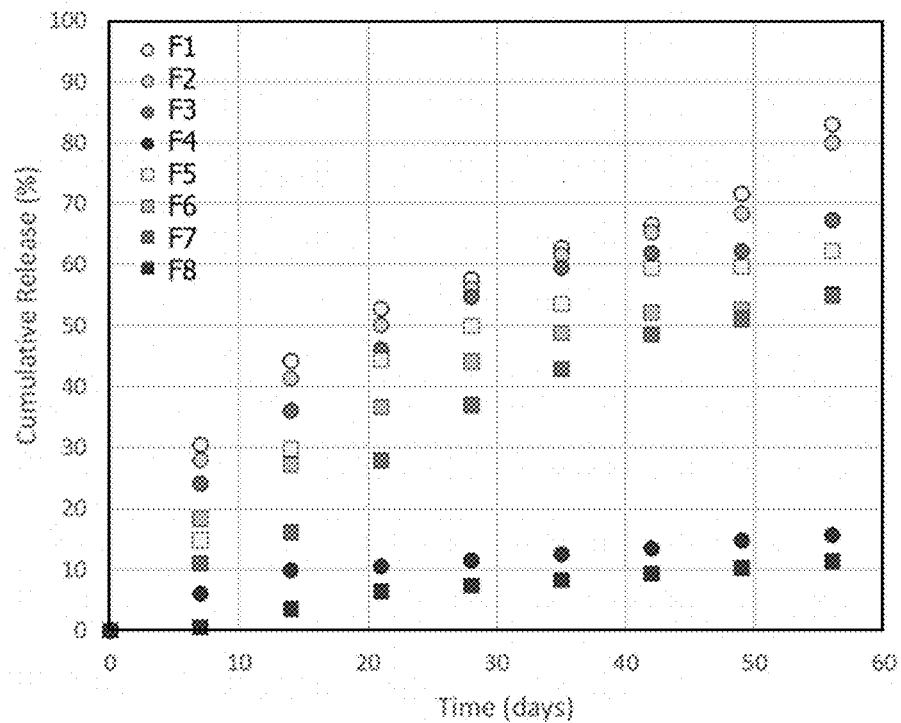
FIG. 17 shows cumulative release curves as percent of API released in vitro for implantable PGSU rod products with 15% to 25% w/w API loadings at different crosslinking densities, for PGSU made from Regenerez® PGS resin.

In some embodiments, an implantable API-loaded PGSU product having a loading in the range of 20% to 40% w/w maintains a substantially-constant release rate in vitro of about 3% per day for a period of more than a month, although API loadings outside this range may also produce similar desirable release results, such as an API loading of 18.2 w/w % or less, as shown in FIG. 16 and FIG. 17.

In some embodiments, an implantable API-loaded PGSU product having a loading of about 3.5% w/w and at a relatively low crosslink density maintains a substantially-constant release rate in vitro of about 0.06% per day for a period of two months.

Exemplary embodiments can be used to create a PGSU biodegradable polymer matrix capable of high solids loading with minimal solvent and heat exposure, capable of being mixed homogeneously, formed via molding, preferably cast molding or injection molding, having mechanical properties sufficient for delivery via a cannula or needle, that provides long-term patient comfort, or combinations thereof.

Exemplary embodiments may create implantable API-loaded PGSU products without exposure to excessive heat, without exposure to solvents, or combinations thereof.

Exemplary embodiments remain within ranges for product-critical parameters that are specific to PGS chemistry that impact PGSU's ability to be a stable, tunable, and reliable drug delivery vehicle.

Exemplary embodiments create a PGSU biodegradable polymer matrix capable of high API loading while maintaining zero order (controlled), near-zero order release characteristics, first-order release characteristics, or near first-order release characteristics over a time period of at least three months.

Exemplary embodiments may have any geometric shape, including, but not limited to, pyramidal, spherical, cylindrical, or cubic, and may include any structure, including, but not limited to, a porous structure, a fibrous structure, and/or a patterned microstructure.

In some embodiments, the implantable product includes a structure to provide ascending release kinetics over the course of weeks to counteract functional tolerance to the API from prolonged exposure. In some embodiments, the implantable product provides ascending, descending, and/or oscillatory release characteristics over a 24-hour cycle that repeats for the lifetime of the implant, such as to provide delivery results similar to a daily oral push-stick osmotic pump, to counteract acute tolerance to the API from repeated exposure.

In some embodiments, the implantable product includes multiple materials, such as, for example, different layers or different zones having different physiochemical properties created by tuning the PGSU, and thus providing different release rates. In some embodiments, the implantable product includes multiple APIs. In some embodiments, the implantable product includes multiple polymers.

Exemplary embodiments provide an API-loaded PGSU implant as an implantable product formed from a PGS resin, an isocyanate, and an API.

Any API may be loaded in the implantable PGSU product. Appropriate types of APIs may include, but are not limited to, therapeutic agents (such as, for example antibiotics, non-steroidal anti-inflammatory drugs (NSAIDs), glaucoma, macular degeneration, and other ophthalmologic medications, angiogenesis inhibitors, drugs to treat diabetes, drugs to treat neurodegeneration, and/or neuroprotective agents), cytotoxic agents, diagnostic agents (such as, for example, contrast agents, radionuclides, fluorescent moieties, luminescent moieties, and/or magnetic moieties), prophylactic agents (such as, for example, vaccines, drugs for human immunodeficiency virus (HIV) prophylaxis and HIV treatment, contraceptive drugs), pain management agents, addiction management agents (such as, for example, opioids, and/or nicotine), plant or herbal extracts (such as, for example, a cannabinoid, such as, for example, tetrahydrocannabinol) and/or nutraceutical agents (such as, for example, vitamins, caffeine, and/or minerals).

Appropriate API therapeutic agents may include, but are not limited to, small molecules, such as, for example, cytotoxic agents; nucleic acids, such as, for example, small interfering ribonucleic acid (siRNA), RNA interference (RNAi), and/or microRNA agents; proteins, such as, for example, growth factors and/or antibodies; peptides; lipids; carbohydrates; hormones; metals; radioactive elements and compounds; drugs; vaccines; and/or immunological agents.

Appropriate API therapeutic agents may additionally or alternatively include, but are not limited to, small molecules with pharmaceutical activity, organic compounds with pharmaceutical activity, clinically-used drugs, antibiotics (such as, for example, penicillin), anti-viral agents, anesthetics, anticoagulants, anti-cancer agents, inhibitors of enzymes (such as, for example, clavulanic acid), promotors of enzymes, steroidal agents, pro-healing agents, pro-polymer degradation agents, anti-oxidants, anti-inflammatory agents, anti-neoplastic agents, antigens, vaccines, antibodies, decongestants, antihypertensives, sedatives, birth control agents, progestational agents, anti-cholinergics, analgesics, anti-depressants, anti-psychotics, β-adrenergic blocking agents, diuretics, cardiovascular active agents, vasoactive agents (such as, for example, epinephrine), anti-glaucoma agents, neuroprotectants, angiogenesis promotors, and/or angiogenesis inhibitors.

Appropriate API antibiotics may include, but are not limited to, β-lactam antibiotics (such as, for example, ampicillin, aziocillin, aztreonam, carbenicillin, cefoperazone, ceftriaxone, cephaloridine, cephalothin, cloxacillin, moxalactam, penicillin G, piperacillin, and/or ticarcillin), macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. The antibiotic may be bacteriocidial or bacteriostatic. Appropriate types of other anti-microbial agents as APIs may include, but are not limited to, anti-viral agents, anti-protazoal agents, and/or anti-parasitic agents.

Appropriate API anti-inflammatory agents may include, but are not limited to, corticosteroids (such as, for example, glucocorticoids), cycloplegics, NSAIDs, and/or immune selective anti-inflammatory derivatives (ImSAIDs).

Appropriate API NSAIDs may include, but are not limited to, celecoxib, rofecoxib, etoricoxib, meloxicam, valdecoxib, diclofenac, etodolac, sulindac, aspirin, alclofenac, fenclofenac, diflunisal, benorylate, fosfosal, salicylic acid including acetylsalicylic acid, sodium acetylsalicylic acid, calcium acetylsalicylic acid, and sodium salicylate; ibuprofen, ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam, indomethacin, nabumetone, naproxen, tolmetin, lumiracoxib, parecoxib, and/or licofelone, including pharmaceutically acceptable salts, isomers, enantiomers, derivatives, prodrugs, crystal polymorphs, amorphous modifications, and/or co-crystals.

Appropriate types of APIs may include, but are not limited to, agents having NSAID-like activity, including, but not limited to, non-selective cyclooxygenase (COX) inhibitors, selective COX-2 inhibitors, selective COX-1 inhibitors, and/or COX-LOX inhibitors, as well as pharmaceutically acceptable salts, isomers, enantiomers, polymorphic crystal forms including the amorphous form, co-crystals, derivatives, and/or prodrugs thereof.

Appropriate APIs may alternatively or additionally include, but are not limited to, adriamycin/bleomycin/vinblastine/dacarbazine (ABVD), avicine, acetaminophen, acetylsalicylic acid, acridine carboxamide, actinomycin, alkylating antineoplastic agent, 17-N-allylamino-17-demethoxygeldanamycin, aminopterin, amsacrine, anthracycline, antineoplastic, antineoplaston, antitumorigenic herbs, 5-azacytidine, azathioprine, triplatin tetranitrate (BBR3464), BL22, bifonazole, biosynthesis of doxorubicin, biricodar, bleomycin, bortezomib, bryostatin, buprenorphine, busulfan, cabotegravir, caffeine, calyculin, camptothecin, capecitabine, carboplatin, chlorambucil, chloramphenicol, cisplatin, cladribine, clofarabine, cyclophosphamide, cytarabine, dacarbazine, dasatinib, daunorubicin, decitabine, dexamethasone, diazepam, dichloroacetic acid, discodermolide, diltiazem, docetaxel, dolutegravir, doxorubicin, epirubicin, epothilone, estramustine, 4'-ethynyl-2-fluoro-2'-deoxyadenosine (EFdA), etonogestrel, etoposide, everolimus, exatecan, exisulind, fentanyl, ferruginol, floxuridine, fludarabine, fluorouracil, 5-fluorouracil, fosfestrol, fotemustine, gemcitabine, hydroxyurea, ibuprofen, idarubicin, ifosfamide, imiquimod, indomethacin, irinotecan, irofulven, ixabepilone, laminvudine, lapatinib, lenalidomide, liposomal daunorubicin, lorazepam, lurtotecan, mafosfamide, masoprocol, mechlorethamine, melphalan, mercaptopurine, metformin, methadone, methotrexate, metoclopramide, mitomycin, mitotane, mitoxantrone, naloxone, naproxen, nelarabine, niacinamide, nicotine, nilotinib, nitrogen mustard, oxaliplatin, first procaspase activating compound (PAC-1), paclitaxel, paracetamol, pawpaw, pemetrexed, pentostatin, pipobroman, pixantrone, polyaspirin, plicamycin, prednisone, procarbazine, proteasome inhibitor, raltitrexed, rebeccamycin, rilpivirine, risperidone, ropinirole, 7-ethyl-10-hydroxycamptothecin (SN-38), salbutamol, salinosporamide A, satraplatin, sildenafil, sirolimus, Stanford V, stiripentol, streptozotocin, swainsonine, tadalafil, taxane, tegafur-uracil, temozolomide, tenofovir, testosterone, tetryzoline, N,N',N''-triethylenethiophosphoramide (ThioTEPA), tioguanine, tolbutamide, topotecan, trabectedin, trazodone, tretinoin, tris(2-chloroethyl)amine, troxacitabine, uracil mustard, valrubicin, vinblastine, vincristine, vinorelbine, vorinostat, zolpidem, and/or zosuquidar.

In exemplary embodiments, PGSU delivers a sustained release of hydrophilic, highly-soluble APIs through a surface erosion mechanism, with a crosslinking that limits burst release, percolation, permeation, and diffusion. Crosslinking density may also be tailored for a particular PGSU degradation rate in order to achieve the desired API release rate.

In exemplary embodiments, PGSU delivers a sustained release of hydrophobic, poorly-soluble APIs through a surface erosion mechanism, with a crosslinking that limits burst release, percolation, permeation, and diffusion. Crosslinking density is also optimized for a particular PGSU degradation rate in order to achieve the desired API release rate.

Thorough PGS chemical characterization may be critical to the development of a successful PGSU product with predictable API delivery behavior. Key physiochemical parameters of the starting polyol that ultimately affect the degradation rate, the release kinetics, and the stability of PGSU have not been previously identified. Namely, polymer architecture, molecular weight, polydispersity index, polycondensation reaction conditions, acid number, hydroxyl number, glycerol-sebacic acid stoichiometry, isocyanate-hydroxyl stoichiometry, and crosslinking density may all affect API pharmacokinetics in final PGSU product form.

PGSU is capable of offering a nearly dose-independent API release, where a higher drug loading does not dramatically impact the relative rate of release of the API. Conventional PGSU drug delivery vehicles do not provide long-term release and do not address applications where 3-month to 12-month therapy duration is needed and extremely high drug loading is necessary in order to maintain the daily therapeutic window for such sustained periods of time. Conventional PGSU drug delivery vehicles do not address drug loading levels or ways to address the challenges of achieving high drug loading levels.

In exemplary embodiments, a PGSU composition accommodates API-loading amounts, based on the total weight of the implantable product, of at least 10% w/w, alternatively 10% w/w to 90% w/w, alternatively 10% w/w to 40% w/w, alternatively 20% w/w to 80% w/w, alternatively at least 20% w/w, alternatively at least 30% w/w, alternatively at least 40% w/w, alternatively 40% w/w to 90% w/w, alternatively 40% w/w to 80% w/w, alternatively 50% w/w to 80% w/w, alternatively 60% w/w to 80% w/w, alternatively up to 90% w/w, or any value, range, or sub-range therebetween, preferably while maintaining substantially zero-order or substantially first-order release while achieving a dose-independent release rate for more than three months, preferably at least six months, inconceivable without the use of a surface-eroding polymer like PGSU and historically unconventional among the commercial space for long-acting implantables.

In exemplary embodiments, a manufacturing process for an API-containing PGSU product from PGS, isocyanate, and the API does not require the use of solvents or heat, which is advantageous for API delivery. The presence of water may quench the isocyanate and prevent effective crosslinking. The PGSU reaction from resin to solid does not require any heat and does not generate any moisture. All components, raw materials, substrates, parts, and surfaces are kept free of moisture. The PGS polyol may be dried to remove any residual moisture remaining from synthesis, whether by drying in an oven, drying in a reactor, or other drying method. This ensures that the desired target crosslinking can be met and no HDI is quenched by water. Conventional PGSU processes do not address the challenges related to drying and degassing PGS resin.

In exemplary embodiments, a manufacturing process for an API-containing PGSU product from PGS, isocyanate, and the API employs the use of vacuum to remove generated air bubbles, entrained air, and entrapped air. Conventional PGSU processes do not address the challenges related to removing air bubbles during mixing and compounding resulting from moisture, dissolved gasses, and mixing.

In some embodiments, a composition includes a PGSU formulation including at least one catalyst to accelerate the PGSU reaction. Appropriate catalysts may include, but are not limited to, catalysts containing metals and/or catalysts of metal salts. Appropriate catalysts may contain or include, but are not limited to, tin, caffeine, potassium, sodium, calcium, magnesium, citric acid, citrate in salt form, such as, for example, potassium citrate, tartaric acid, and/or tartrate in salt form, such as, for example, potassium tartrate. The organic acid form of citric acid and tartaric acid may participate in crosslinking, while the salt form of citrate and tartrate may not participate in crosslinking. Appropriate catalysts may be non-toxic, pharmaceutically-friendly, and/or non-interfering with respect to the pharmacokinetics of the PGSU. Catalysts that are salt-based may offer improved biocompatibility, non-toxicity, pharmacokinetic compatibility, and pharmaceutical acceptance compared to heavy metal-based catalysts, which have strict limits of exposure in humans.

In some embodiments, an implantable product includes a PGSU formulation including at least one additive to improve API release kinetics, improve API solubility, improve API permeability, improve product stability, improve product radiopacity, improve PGSU crosslinking kinetics, improve PGSU working time, improve rheological behavior, improve thermal behavior, improve mold release, or combinations thereof. Appropriate additives may include, but are not limited to, PGS flour, mannitol, lactose, magnesium stearate, sodium stearate, stearic acid, poly(ethylene glycol) (PEG), triethyl citrate (TEC), barium sulfate, solubility enhancers, permeability enhancers, plasticizers, fillers, binders, disintegrants, catalysts, microparticles, nanoparticles, or combinations thereof.

As used herein, "PGS flour" refers to a thermoset PGS that has been processed, such as, for example, micronized by grinding, into a powder of fine particle size, such as, for example, less than 1000 microns, such as, for example, as disclosed in U.S. Patent Application Publication No. 2017/0246316, which is hereby incorporated by reference in its entirety.

In some embodiments, a composition includes an isocyanate having an aliphatic chemical structure.

In some embodiments, a composition includes an isocyanate having an aromatic chemical structure.

In some embodiments, a composition includes an isocyanate having a combination aliphatic-aromatic chemical structure.

In some embodiments, a composition includes blocked isocyanates that become unblocked upon exposure to a trigger, such as, for example, heat, in order to extend the working time and subsequently improve the homogeneous API incorporation and the reactant mixing. Blocked isocyanates may be used to delay the reaction until a particular temperature or other trigger or benchmark is reached. This allows control over when and where the reaction occurs, as opposed to the reaction beginning at the moment of formulation. This strategic delay grants a longer pot life, affording more time for mixing and more time for forming, all of which assist manufacturing by offering more freedom in the choice of manufacturing technique, de-risking the compounding step, de-risking the molding or extrusion step, allowing more homogeneous mixing, allowing more homogeneous crosslinking, simplifying the manufacturing process, saving time, and/or saving cost. The ability to trigger the reaction using a blocked isocyanate may also protect the API from cross-reaction into the polymer during crosslinking.

In some embodiments, a composition includes an isocyanate-to-hydroxyl stoichiometric ratio in the range of 1:0.25 to 1:2, alternatively in the range of 1:0.25 to 1:0.75, alternatively in the range of 1:0.4 to 1:0.75, alternatively in the range of 1:0.25 to 1:1, alternatively in the range of 1:0.25 to 1:1.25, alternatively in the range of 1:0.25 to 1:1.5, or any value, range, or sub-range therebetween, to maintain a stable product with optical clarity that does not exhibit clouding, hazing, blooming, or stiffening over time upon storage at ambient conditions including room temperature, atmospheric pressure, and room humidity. Certain isocyanate-to-hydroxyl stoichiometric ratios less than 1:2, such as, for example, 1:3 or 1:4, were found to suffer from clouding and stiffening when stored in ambient conditions, which is detrimental to product shelf life. Additionally, conventional intravitreal injections and implants made of other polymers require cold storage at −4° C. or −20° C., which may be costly and/or impractical for drug products.

In some embodiments, a composition includes a polyol reactant composed of at least 50% and up to 100% w/w solids content to minimize or eliminate the use of solvents.

In some embodiments, a composition includes an API loading into any component, partial blend, or complete blend of the PGSU formulation to create an implantable PGSU product with up to 90% w/w API content that achieves a greater than 3-month duration of drug therapy.

In some embodiments, a composition includes a PGSU formulation with rheological properties amenable to mixing, incorporation of an API, and manufacturing methods.

In some embodiments, a composition includes a PGSU formulation where no partitioning of API occurs within the polymer matrix due to the API having a strong physical affinity for the matrix chemistry.

In some embodiments, a composition includes a crosslinking density of polymerized PGSU of at least 0.8 mol/L, alternatively between 0.8 mol/L and 4.0 mol/L, alternatively between 0.8 mol/L and 3.5 mol/L, alternatively at least 1.0 mol/L, alternatively between 1.0 mol/L and 4.0 mol/L, alternatively between 1.0 mol/L and 3.5 mol/L, alternatively between 1.0 mol/L and 3.0 mol/L, alternatively between 1.0 mol/L and 2.0 mol/L, alternatively between 1.5 mol/L and 4.0 mol/L, alternatively between 1.5 mol/L and 3.5 mol/L, alternatively between 2.0 mol/L and 4.0 mol/L, alternatively between 2.0 mol/L and 3.5 mol/L, alternatively between 2.5 mol/L and 3.5 mol/L, alternatively between 3.0 mol/L and 3.5 mol/L, or any value, range, or sub-range therebetween.

In some embodiments, a composition includes a crosslinking density of polymerized PGSU between 0.5 mol/L and 3.5 mol/L, to minimize, reduce, or eliminate clouding and hazing during shelf life storage.

In some embodiments, a composition includes a crosslinking density of polymerized PGSU between 1.5 mol/L and 3.5 mol/L, to minimize, reduce, or eliminate permeation, percolation, burst release, and/or diffusion.

In preferred embodiments, PGSU has a swellability below 5% w/w in saline solution at 23° C. or 37° C. over the course of two weeks, which reduces permeation, percolation, burst release, and diffusion in a highly API loaded implant. Conventional processes describe swelling to be 5-10% w/w in saline solution at 37° C. for 24 hours for solvent-based PGSU at lower crosslinking densities than described here. Conventional processes, aiming to improve water uptake by PGSU by incorporating drug loading rather than decrease water uptake by PGSU with high drug loading, describe swelling to be 5% w/w, 30% w/w, and 80% w/w in saline solution for 24 hours for solvent-free PGSU, solvent-free PGSU loaded with 25% w/w BSA, and solvent-free PGSU loaded with 25% w/w BSA-trehalose, respectively, at lower crosslinking densities than described herein.

In preferred embodiments, PGSU has a sol content below 5% w/w under 24 hours of tetrahydrofuran (THF) swelling, which is important to reduce extractables, reduce blooming of sol fractions to the surface, reduce API migration to the surface, reduce burst release, prolong shelf life stability, and prevent biocompatibility issues. Conventional processes describe sol content to be 10-20% w/w under 24 hours of ethanol swelling for solvent-based PGSU at lower crosslinking densities than described herein.

Engineering properties of preferred forms of an implantable product for delivery and in vivo service may include a flexible, elastomeric product, as indicated by hardness, flexural modulus, compressive modulus, and tensile modulus, that reduces patient discomfort, reduces propensity for fracture during normal patient movement, conforms to anatomical geometry, such as, for example, anatomical topography or curvature, and closely matches the mechanical properties of human tissue at the implant location, such as the inner upper arm where adipose and muscle tissue can vary greatly based on gender, age, race, fitness level, hydration level, and pre-existing health conditions. Having an implant with mechanical properties that minimize compliance mismatch with native tissue may temper inflammatory response and prevent fibrosis.

Other engineering properties of preferred forms of an implantable product for delivery and in vivo service may include an easily deliverable product without high friction, buckling, or kinking during deployment from a delivery device.

In preferred embodiments, unloaded PGSU has a flexural modulus greater than 4 MPa, an elastic compressive modulus greater than 25 MPa, and an elastic tensile modulus greater than 4 MPa. Conventional processes describe an elastic tensile modulus less than 10 MPa for solvent-free PGSU and less than 20 MPa for solvent-based PGSU, and elongations up to 125% for solvent-free PGSU and up to 520% for solvent-based PGSU. To obtain theses values in conventional processes, all PGSU samples were immersed in saline for 24 hours at 37° C. prior to testing, which removes the unreacted low molecular weight fractions that otherwise serve as plasticizer, and solvent-based PGSU samples were additionally immersed in ethanol for 24 hours to intentionally swell the matrix and remove sol content, which similarly serves as plasticizer (see Pereira et al., "A Highly Tunable Biocompatible and Multifunctional Biodegradable Elastomer", Adv. Mater., Vol. 25, pp. 1209-1215, 2013). Accordingly, these conventional process mechanical property values reflect a stiffer PGSU than PGSU without any processing, and as such cannot be directly compared to mechanical property values described herein. Conventional processes aimed to improve the tensile elongation and tensile cycling of PGSU, not optimize flexural properties best for patient comfort and implant deployment like described herein. Loaded PGSU, however, may have a significantly different flexural modulus, elastic compressive modulus, and elastic tensile modulus.

Other engineering properties of preferred forms of an implantable product for delivery and in vivo service may include surface erosion as the mechanism of API release in order to achieve a release rate that is independent of API loading concentration.

Other engineering properties of preferred forms of an implantable product for delivery and in vivo service may include a product with initial water-impermeability, in order to eliminate API release that is driven by a concentration gradient between the polymer matrix and surrounding environment.

Other engineering properties of preferred forms of an implantable product for delivery and in vivo service may include a product that may be tuned to a desired degradation rate and corresponding API release rate using the physiochemical properties of the PGSU. Such physicochemical properties may include, but are not limited to, the glycerol-to-sebacic acid stoichiometric ratio, the hydroxyl number, the acid number, the isocyanate-to-hydroxyl stoichiometric ratio, the molecular weight, the crosslinking density, or combinations thereof.

Other engineering properties of preferred forms of an implantable product for delivery and in vivo service may include a duration of therapy greater than 3 months while maintaining plasma concentrations in a therapeutic window, afforded by a high drug loading in combination with the surface erosion of PGSU.

Other engineering properties of preferred forms of an implantable product for delivery and in vivo service may include a reduced lag upon the start of therapy and a reduced tail upon the end of therapy, afforded by surface erosion of PGSU.

Other engineering properties of preferred forms of an implantable product for delivery and in vivo service may include retrievability for greater than one month post-implantation, in the event of an adverse reaction, for example.

Other engineering properties of preferred forms of an implantable product for delivery and in vivo service may include PGSU or biodegradation byproducts that do not interfere with API absorption, distribution, metabolism, excretion characteristics, or combinations thereof.

Other engineering properties of preferred forms of an implantable product for delivery and in vivo service may include PGSU or biodegradation byproducts that do not impact API solubility, permeability, hygroscopicity, thermal stability, hydrolytic stability, photostability, or combinations thereof.

Other engineering properties of preferred forms of an implantable product for delivery and in vivo service may include PGSU or biodegradation byproducts that do not modify an API free acid, an API free base, an API salt form, an API crystallinity, an API amorphism, or combinations thereof and/or do not induce any polymorphic changes.

Other engineering properties of preferred forms of an implantable product for delivery and in vivo service may include PGSU or biodegradation byproducts that are non-immunogenic and that do not incite an inflammation that would interfere with the API release rate.

A deployment method and mode may provide a product assembled into a delivery device, such as, for example, a needle, a cannular, an applicator, a trocar, or combination thereof.

A deployment method and mode may provide deployment of an implantable product with the application of a local anesthetic.

A preferred process may include reacting a polyol and an isocyanate together using a compounding method that eliminates any air voids. A preferred process may include incorporation of the API pre-reaction, using compounding methods to allow API loading up to 90% w/w solids. Appropriate compounding methods may include, but are not limited to, static mixing, shear mixing, vacuum mixing, twin screw mixing, venturi mixing, or combinations thereof.

A preferred process may include incorporating the API post-reaction, using an infusion method and/or protecting the API during incorporation pre-reaction, in order to prevent cross-reaction of API into the PGSU matrix during polymerization, in the event an API has susceptible and sterically-accessible functional groups that may participate in covalent bond formation, which may either affect API bioavailability or PGSU crosslinking and degradation.

A preferred product manufacturing process may include reaction injection molding, casting, molding, spray coating, spin coating, electrospinning, additive manufacturing, extrusion, or combinations thereof.

A preferred product manufacturing process may include using a die with a gradient or particular architecture that is designed to achieve specific API release kinetics.

A preferred product manufacturing process may include forming a cylindrical rod-shaped product with a higher API loading in the center, in order to achieve a more linear first-order API release rate, as the diameter decreases during surface erosion of PGSU. In contrast, a first order release rate is better maintained for rectangular film shapes, as the thickness decreases during PGSU surface erosion.

A preferred product manufacturing process may include using mild shear and friction conditions that do not affect API properties.

A preferred product manufacturing process may include solvent evaporation that is limited, slowed, or controlled to prevent API aggregation, phase separation, or partitioning during the solvent evaporation step.

A preferred product manufacturing process may include solvent evaporation post-reaction at low heat conditions, such as less than 60° C. (140° F.), that do not affect API properties in cases where a solvent is employed in the process, such as to reduce viscosity.

A preferred product manufacturing process may include application of low heat conditions, such as less than 40° C. (104° F.), that do not affect API properties in cases where heat is employed in the process, such as to reduce viscosity.

In other embodiments, the product manufacturing process may include cooling conditions, such as less than 20° C. (68° F.), before, during, or after mixing, to slow the reaction and avoiding or reducing the likelihood of clogging the injection molding equipment.

A preferred product manufacturing process may preserve all constraints on stoichiometry, degradation rate, and tissue compliance properties of a PGSU composition.

A preferred product manufacturing process may include the compounded level of API remaining present at a prescribed level, within United States Pharmacopeia (USP) standards, following the manufacturing process.

Exemplary embodiments provide predictable and reliable API release kinetics across PGSU chemical parameters as well as at different drug loadings. In exemplary embodiments, the implantable product includes a PGSU cylindrical rod formed from a highly-branched PGS resin created from a water-mediated polycondensation reaction. In some embodiments, the PGS resin includes a polydispersity index of about 8, a molecular weight of about 15,000 Da, an acid number of about 43, a hydroxyl number of about 200, and about 1:1 stoichiometric ratio of glycerol-to-sebacic acid. The PGS resin is warmed to about 37° C. (98.6° F.) and homogeneously mixed under vacuum with about 60% w/w API, followed by further homogeneous mixing under vacuum with about 0.1% w/w tin(II) 2-ethylhexanoate catalyst. A flowable resin is created without a solvent. Alternatively, a PGS solution may be prepared at about 60% w/w in 1:1 (w/w) acetone-to-propyl acetate solvent in order to achieve flowability at about 23° C. (73.4° F.) and to increase the working time. The PGS-API-catalyst blend is then combined with aliphatic HDI at an isocyanate-to-hydroxyl stoichiometric ratio of about 1:0.6 using vacuum mixing. The mixture is then quickly transferred into a syringe and then injected into a 2-mm to 3-mm inner diameter tubing to cast the final cylindrical rod form. The set-to-touch time is a few minutes, and the filled molds are kept at about 23° C. (73.4° F.) for about 24 hours to set fully. The crosslinking is complete once substantially all of the HDI has been reacted, and additional processing is not necessary. In processes using solvent to improve PGS flowability, the rods are placed in a 40° C. (104° F.) oven for about 6 days to ensure complete solvent evaporation to below 0.5% w/w loss on drying after the initial 24 hours at about 23° C. (73.4° F.).

In exemplary embodiments, the reaction injection molding parameters are selected to achieve solvent-free, low-temperature, high-throughput manufacture with homogeneous compounding across a range of viscosities. The throughput of a reaction injection molding system may be dependent on die design and parallelizability of injection. Homogeneous blending and API incorporation may be dependent on the viscosity, the flow rate into the mixing chamber, and the method of mixing. In exemplary embodiments, the API and the catalyst are pre-mixed into the PGS resin, and mixing is maintained as the material is routed to a mixing chamber, where it is combined with isocyanate within seconds and quickly injected under pressure into a die for forming.

In exemplary embodiments, a two-component mixing and metering unit for PGSU reaction injection molding includes two positive displacement metering pumps with flow and ratio adjustability, such as, for example, a servo-controlled progressive cavity or servo-controlled spur gear with volumetric proportioning; two supply vessels of suitable capacity for material feeding, such as, for example, pressurized tanks with band heaters, electric agitators, and vacuum kits; a static or dynamic mixing applicator, such as, for example, a dynamic mixing valve with circulation of both components, drive unit with pneumatic motor, non-return valves, and pneumatic and hydraulic fittings; a vacuum pump with control interface, such as, for example, a vacuum pump with vacuum sensors on all tanks and pneumatically operated valves; and an electronic control package.

In some embodiments, PGSU may be extruded using a single screw extruder, a twin screw extruder, a microcompounder, a dual-barrel cartridge, single batch reaction injection molding, or continuous recirculating reaction injection molding. Mixing of one or more components may occur prior to introduction to the compounding equipment, such as, for example, using a speedmixer, an overhead mixer, a dynamic mixer, a high-shear mixer, and/or a 3-roll mill. One or more mixing steps may occur in the barrel, tubing, chamber, tip, and/or nozzle of the compounding equipment and may be either static or dynamic. Addition of the isocyanate into the various equipment is carefully designed, since homogeneous isocyanate incorporation is desirable for even crosslinking, and the isocyanate and catalyst should be kept physically separated until it is desired to initialize the PGSU reaction. In some embodiments, the PGSU reaction may begin to occur inside the equipment, but the material will not become solid or semi-solid until it has exited the equipment, allowing for the PGSU blend to remain liquid, flowable, and mixable inside the equipment. In some embodiments, the PGSU reaction mixture may be recirculated inside the equipment until the monitored viscosity reaches a designated point, after which the PGSU blend is allowed to exit the equipment. In some embodiments, the PGSU reaction does not occur until the isocyanate and catalyst components meet in a mixing chamber, a tip, or a nozzle, and prior to this point the isocyanate and catalyst are kept physically separated. In some embodiments, the PGSU reaction does not occur until the PGSU blend exits the equipment. In some embodiments, the PGSU may be fabricated using heat to accelerate and properly time the curing at the point of exit from the nozzle or die. The PGSU may be drug-loaded at the time of forming. Alternatively, the PGSU may be infused or soaked with API after forming.

In some embodiments, high shear mixing is required to evenly distribute and fully incorporate isocyanate into the PGS resin, such as, for example, by using mixing media and/or grinding media in concert with other mixing methods, such as, for example, using a speedmixer, an overhead mixer, a dynamic mixer, a high-shear mixer, and/or a 3-roll mill. Mixing may also occur in the compounding equipment, such as, for example, a single screw extruder, a twin screw extruder, a microcompounder, a dual-barrel cartridge, single batch reaction injection molding, or continuous recirculating reaction injection molding, where mixing may occur in the barrel, tubing, chamber, tip, and/or nozzle and may be either static or dynamic. Homogeneous distribution and complete incorporation of isocyanate into the PGSU blend is challenging due to the disparate viscosities of isocyanate and PGS resin, the high volumes of isocyanate in order to achieve high crosslinking densities, and the immiscibility of isocyanate with PGS resin. However, homogeneous distribution and complete incorporation of isocyanate is desirable in order to achieve the target crosslink densities and PGSU degradation rates needed for sustained drug release.

In some embodiments, high shear mixing is desirable to evenly distribute and fully incorporate API into the PGS resin, for example, by using mixing media and/or grinding media in concert with other mixing methods, such as, for example, using a speedmixer, an overhead mixer, a dynamic mixer, a high-shear mixer, and/or a 3-roll mill. Mixing may also occur in the compounding equipment, such as, for example, a single screw extruder, a twin screw extruder, microcompounder, a dual-barrel cartridge, single batch reaction injection molding, or continuous recirculating reaction injection molding, where mixing may occur in the barrel, tubing, chamber, tip, and/or nozzle and may be either static or dynamic. Homogeneous distribution and complete incorporation of API into the PGSU blend is challenging due to the high viscosity of PGS resin, bulk density of APIs, large masses of API necessary to achieve high drug loadings, and sometimes poor wettability of APIs by PGS resin. However, homogeneous distribution and complete incorporation of API is desirable to achieve the target drug loading, content uniformity, and particle distribution needed for sustained drug release.

In some embodiments, heat may be applied to reduce PGS viscosity so that PGS components are flowable and manufacturable and so that homogeneous mixing with isocyanate and API may be achieved. PGS blended with isocyanate was found to prematurely solidify, even in the absence of catalyst, if exposed to temperatures greater than 60° C. for more than a few minutes. PGS blended with isocyanate was found to prematurely solidify, even in the absence of catalyst, if held at 23° C. for 24 hours. PGS blended with isocyanate was found to prematurely solidify, even in the absence of catalyst, if held at −20° C. for greater than 48 hours. Thus, PGS blended with isocyanate, in the absence of catalyst, is best maintained below 40° C. and used within a few hours of mixing. In some embodiments, heat may be applied to accelerate or time the PGSU reaction. Due to the importance of heat for viscosity reduction and/or reaction timing, torque rheology trials were performed on PGS resin blended with isocyanate and catalyst to determine how the PGSU reaction kinetics change across temperatures ranging from 40° C. to 80° C.

In some embodiments, heat may be applied after forming PGSU into a solid in order to force complete reaction of the isocyanate since residual isocyanate has been linked with irritation and sensitization in vivo. This is especially important at high crosslinking densities where the isocyanate is present in excess of the polyol, such as, for example, when isocyanate-to-hydroxyl stoichiometric ratios are between 1:0.25 and 1:0.9. It was found that heating PGSU implants at 40° C. immediately after forming or 24 hours after forming helped drive the isocyanate to react completely, leaving no residual isocyanate behind after 24 hours of this mild heat exposure. Without added heat, at 23° C., this process of fully reacting the isocyanate required 72 to 96 hours.

In other embodiments, PGS resin, catalyst, and isocyanate form PGSU in an additive manufacturing application, such as a three-dimensional (3D) printing application. Various additive manufacturing methods, including, but not limited to, fused deposition modeling, selective laser sintering, material extrusion, bioprinting, stereolithography, digital light processing, digital light synthesis (continuous liquid interface production), inkjet printing, or material jetting, may be suitable for PGSU, depending on the chemistry, viscosity, and polymerization kinetics. In some embodiments, a dual barrel 3D printer combines the PGS-API-catalyst blend with HDI right at the nozzle prior to layer extrusion. In some embodiments, a single barrel 3D printer directs a PGSU formulation with a working time greater than the time needed to print an entire barrel volume, such as, for example, 20 minutes for a 10-cc syringe volume. Fillers and/or plasticizers may be included to modify the PGSU formulation viscosity, and API incorporation may impact the rheology as well. The ability to additively manufacture PGSU opens many other possibilities, such as, for example, patient-specific implantable products and designs, complex geometries with internal struts and voids, manufacturing-on-demand to reduce a stability testing burden and equipment costs, and multi-material constructs with co-delivery of multiple APIs having different release kinetics from tuned PGSU formulations.

In other embodiments, PGSU formulations for sustained release may be composed of complex geometries with different compartments, such as core-sheath rods, where the sheath acts as a barrier to prevent diffusion or burst release, or where the sheath is loaded with drug to provide an initial purposeful burst release to reach therapeutic plasma concentrations quickly. Different compartments may contain different APIs or different API concentrations or have different crosslinking densities to achieve different degradation rates. Multi-compartment, multi-modal, or multi-drug PGSU designs may be used for drug delivery through transdermal, parenteral, subcutaneous, intramuscular, intraocular, intravitreal, intraarticular, intravaginal, buccal, or gastrointestinal routes of administration.

In other embodiments, PGSU complex geometries may include microparticles, nanoparticles, microspheres, nanospheres, multi-layered spheres, multi-compartment particles, and/or shaped particles for the purpose of drug delivery through transdermal, parenteral, subcutaneous, intramuscular, intraocular, intravitreal, intraarticular, intravaginal, buccal, or gastrointestinal routes of administration. PGSU microspheres may be fabricated using a dual-chamber spray coater nozzle and spraying the blended PGSU formulation into air, onto a substrate, or into a solvent, for size control and collection. PGSU microspheres may be fabricated using emulsion technology and heat to accelerate and properly time the curing. PGSU microspheres may be unloaded or drug-loaded and may be fabricated across a variety of crosslinking densities. PGSU microspheres may be infused or soaked with API after forming. PGSU microspheres may be coated with API powder, API solution, or an API-polymer blend after forming. PGSU microspheres may be fused together after being formed to create various shapes. PGSU microspheres may be formulated to aggregate or cluster together once injected into the body, to create a depot for sustained release.

In other embodiments, PGSU complex geometries may include fibers, yarns, knits, weaves, braids, and/or fibrous mats, using, for example, extrusion, wet spinning, fiber drawing, fiber pulling, or electrospinning. PGSU fibers may be extruded using a single screw extruder, a twin screw extruder, a microcompounder, a dual-barrel cartridge, single batch reaction injection, or continuous recirculating reaction injection. In some cases, PGSU fibers may be fabricated using heat to accelerate and properly time the curing at the point of exit from the nozzle or die. PGSU fibers may be drug-loaded at the time of forming. Alternatively, PGSU fibers may be infused or soaked with API after forming. Drawing down PGSU fibers may convey an orientation of the polymer chains, before the curing is complete, which allows better surface properties, higher strength, more homogeneous mesh size, more controlled drug release, more controlled degradation, and/or less inflammatory response. In some embodiments, PGSU fibers may have a circular cross-section. Alternatively, PGSU fibers may have a shaped cross-section that dictates PGSU degradation behavior, drug loading efficiency, and drug release kinetics. PGSU's surface erosion changes with fiber cross-section shape due to surface area-to-volume ratio changes, since water and enzymes need to have access to the polymer before hydrolytic and enzymatic degradation can occur, respectively. Drug diffusion out of the matrix changes with fiber cross-section shape due to the different path lengths in the matrix that the drug travels through during release. Drug adsorption onto the matrix during loading changes with fiber cross-section shape due to different surface areas being exposed during coating. Drug infiltration into the matrix changes with fiber cross-section shape due to different surface areas being exposed and different path lengths in the matrix that the drug travels through during infusion or soaking. All of these phenomena result in a drug release that is dependent on fiber cross-section shape. The result is a highly-tunable system where drug loading, drug release, and/or polymer degradation may be augmented by merely changing the shape of the die during PGSU fiber extrusion.

In other embodiments, PGSU complex geometries may include microneedles and microneedle patches for the purpose of drug delivery through transdermal, parenteral, subcutaneous, intramuscular, intraocular, intravitreal, intraarticular, intravaginal, buccal, or gastrointestinal routes of administration.

In other embodiments, PGSU may be combined with textile technology to create textile patches, wearable textiles integrated into clothing, textile sensors, or implantable textiles for the purpose of drug delivery through transdermal, parenteral, subcutaneous, intramuscular, intraocular, intravitreal, intraarticular, intravaginal, buccal, or gastrointestinal routes of administration.

In other embodiments, PGSU may be formulated for in situ gelation, where a dual-barrel cartridge keeps the isocyanate and catalyst physically separated until the two components meet in a mixing chamber, tip, or nozzle, and the PGSU blend is delivered into the body. The timing of the cure, for example, may be slow or rapid, may be driven by urethane chemistry or ionic interactions with the in vivo environment, and/or may produce a liquid, semi-solid, or solid depot for drug delivery, tissue regeneration, cellular infiltration, cellular delivery, lubrication, viscosupplementation, mechanical dampening, mechanical support, mechanical blocking, anti-inflammatory treatment, and/or anti-bacterial treatment.

In other embodiments, PGSU may be made into a foam or porous scaffold using a controlled gas-foaming process. Air bubbles may be introduced by purposefully introducing moisture during the PGSU reaction. Alternatively, air bubbles may be introduced by mixing PGSU with high shear in the absence of vacuum, causing air entrainment. Alternatively, air bubbles may be introduced by extruding PGSU with a twin screw extruder, which is typically run with open headspace, causing air entrainment. Alternatively, air bubbles may be introduced into PGSU by formulating in a surfactant or an air-entraining agent.

In other embodiments, PGSU is intended to be solid without any air bubbles or voids. Air bubbles may be eliminated by performing dispensing, mixing, compounding, and/or forming steps under vacuum to avoid air entrainment. Alternatively, the pouring, filling, molding, or forming process may be performed under vacuum to avoid air entrapment, which causes large bubbles and voids. Alternatively, air bubbles may be eliminated by dispensing, mixing, compounding, and/or forming under centrifugation. Alternatively, air bubbles may be eliminated by performing dispensing, mixing, compounding, and/or forming under sonication. Alternatively, air bubbles may be eliminated by formulating in a surfactant, degassing agent, or moisture removal agent. Alternatively, air bubbles may be eliminated by using low-viscosity components, such as, for example, solvated PGS or heated PGS to reduce viscosity, which allows air bubbles to self-eliminate and flow out more easily. Alternatively, air bubbles may be eliminated by using low shear mixing, since high shear mixing may cause air entrainment and air bubble coalescence. Alternatively, air bubbles may be eliminated by using high shear mixing under vacuum. Alternatively, the PGSU reaction may be driven more quickly using heat to prevent air bubble coalescence. Alternatively, air bubbles may be eliminated by keeping all components, raw materials, substrates, parts, and surfaces degassed and free of moisture. PGS resin is formed by a polycondensation reaction which inherently produces some water; however, this moisture may be removed with vacuum during PGS resin synthesis. The PGS polyol may be dried further to remove any residual moisture remaining from synthesis, whether by drying in an oven, drying in a reactor, or drying by another drying method. The method of PGS resin synthesis, whether using a water-mediated process or not, may impact the residual moisture and dissolved gasses in the PGS resin. Parameters such as stirring speed, stirring blade design, reactor dimensions, nitrogen flow rate, vacuum pressure, reaction duration, reaction temperature, reactor insulation, ambient temperature, solubility of starting materials glycerol and sebacic acid, order of addition of starting materials glycerol and sebacic acid, and/or timing of addition of starting materials glycerol and sebacic acid may all impact residual moisture content and dissolved gasses content.

In other embodiments, PGSU geometries may have small or large molecule APIs conjugated, tethered, tethered with a cleavable linkage, nonspecifically adsorbed, ionically complexed, embedded, encapsulated, or otherwise located on the PGSU surface, located within the PGSU matrix, or located within various PGSU compartments and geometries, resulting in different drug release rates. PGSU degradation rate may be tailored to achieve different surface erosion timelines, for example, by tailoring the glycerol-to-sebacic acid stoichiometric ratio, isocyanate-to-hydroxyl stoichiometric ratio, and/or molecular weight, which may confer complex drug release profiles when combined with these various drug-loading techniques. Agents that accelerate or decelerate degradation, for example, by activating and/or recruiting enzymes and/or macrophages, may also be included in specific compartments to further refine the PGSU degradation profile. Agents that dampen or hinder inflammation may also be included in specific compartments to modulate inflammatory response throughout various stages of the implant lifetime.

In other embodiments, a cleavable linkage may be incorporated into the PGSU polymer backbone to provide additional scission sites for controlled degradation, such as, for example, enzyme-mediated degradation. The cleavable linkage may be a peptide sequence that acts as a binding and cleavage site for a general enzyme, such as lipase or esterase, or a site-specific enzyme, such as matrix metalloproteinase-2 (MMP-2) or matrix metalloproteinase-9 (MMP-9).

In other embodiments, PGSU may be blended with other elastomers, such as, for example, silicone, polyurethane, thermoplastic polyurethane, and/or EVA, to lend biodegradable behavior to these otherwise non-degradable polymers.

In other embodiments, PGSU may be blended with thermoplastics, such as, for example, PLA, PGA, PLGA, PCL, and/or PEG, to lend softness, compliance, and elasticity to these otherwise stiff degradable polymers, and to lend surface-eroding properties to these otherwise bulk eroding polymers.

In other embodiments, PGSU may be blended with PGS crosslinked by other mechanisms, such as, for example, thermosetting, cationic UV curing, acrylate UV curing, visible-light curing, infrared-light curing, microwave curing, any other electromagnetic radiative curing, ionic gelation, 1-ethyl-3-(3-dimethylaminopropyl)carbodiimide (EDC) chemistry, EDC/N-hydroxysuccinimide (NHS) chemistry, and/or click chemistry. Alternatively, PGSU may be blended with uncured PGS resin. Alternatively, PGSU may be blended with PGS flour, which is created by thermosetting PGS and cryomilling down to a predetermined particle size.

In other embodiments, PGSU's surface erosion behavior allows the implant to be retrievable for a much longer proportion of the implant lifetime, compared to bulk eroding polymers, which become soft and diffuse throughout the implant volume early on, since surface eroding PGSU remains in one piece until the very end of its degradation pattern. Retrievability is important in the instance where a patient has an adverse reaction to the API or polymer, needs to receive oral or intravenous therapy that is contraindicated with the drug delivered by the implant, needs to receive oral or intravenous therapy that cannot additively stack with the dose delivered by the implant, or otherwise needs emergency removal of the implant for any reason.

In other embodiments, PGSU's surface erosion behavior allows a rapid onset of degradation at the end of the implant lifetime, avoiding the tail effect that commonly affects non-eroding polymers and avoiding dose dumping that commonly affects bulk eroding polymers. In non-degradable implants, plasma API concentrations eventually become sub-therapeutic after most of the API has diffused out, leaving behind a very weak API concentration gradient, which causes diffusion of the final amount of API to occur very slowly. This tail effect may last weeks, and if the bulk eroding implant is not retrievable at this point, the patient is unprotected or untreated during these weeks until a new implant can safely be deployed without any risk of additive dose stacking. Moreover, the API itself may have a very long wash out period, which adds further delay in protection or treatment until a new implant can be administered. In bulk-eroding implants, the polymer matrix eventually becomes diffuse throughout its volume and all the remaining API diffuses out at once. This dose dumping can lead to super-therapeutic and even dangerous plasma API concentrations. With surface eroding implants like PGSU, at the end of the implant lifetime, the API concentration gradient is still strong, since the distribution of API in the center core is the same as the outside edge, if homogeneous mixing has been achieved. At the point where only a small section of the implant is left following steady erosion, for example, the width of two or three API particles, the remaining API may quickly diffuse out, leaving behind a highly porous section of implant with an incredibly high surface area. Since the rate of hydrolytic and enzymatic degradation increases with increasing surface area, having a highly porous PGSU triggers a rapid erosion to 100% degradation. The benefit of hydrophobic, surface-eroding PGSU is that this rapid onset degradation does not occur until the majority of the implant volume has already eroded away, since water cannot otherwise access the implant interior.

In preferred embodiments, PGSU with high crosslinking, such as, for example, an isocyanate-to-hydroxyl stoichiometric ratio between 1:0.25 and 1:1.25, results in an implantable polymer with reduced inflammatory response, complement activation, cellular attachment, and/or fibrous encapsulation compared to less crosslinked PGSU, due to fewer free functional groups present on the surface, such as, for example, free carboxylate groups that are known to activate complement factors. Increasing the crosslinking density of PGSU increases the incidence of bond formation between functional groups, reducing the number of free, unbound functional groups that may aggravate and/or activate immune cells, circulating cells, and/or local cells. Reducing or eliminating a persistent inflammatory response leads to lower incidence of fibrosis and/or fibrous encapsulation, which otherwise hinders drug release rates, drug permeation into target tissues, drug distribution within target tissues, patient comfort, patient mobility, implant retrieval, and/or implant location identification. Particularly as the PGSU surface erodes, if the high degree of crosslinking is homogeneous throughout the implant volume and the cleaved bonds that become exposed during degradation are benign, the PGSU implant material remains biocompatible and non-inflammatory throughout the lifespan of the implant, leaving behind minimal changes to the underlying tissue once 100% degradation is reached. Conventional processes describe how increasing PGSU crosslinking reduces cell attachment after 24 hours from 50% to 20%, when crosslinking is increased from an isocyanate-to-hydroxyl stoichiometric ratio of 1:5 to a ratio of 1:1.5. In preferred embodiments, PGSU with an isocyanate-to-hydroxyl stoichiometric ratio between 1:0.25 and 1:1.25 may have further reduced cell attachment, creating a PGSU implant that has minimal biological interaction with surrounding tissues and a more efficient drug release that is unhindered by cellular attachment and growth. Conventional processes also demonstrate foreign body response, inflammatory cell infiltration, and fibrous encapsulation persisting from 1 week through 40 weeks for PGSU with lower crosslinking densities having an isocyanate-to-hydroxyl stoichiometric ratio in the range of 1:1.5 to 1:5. In preferred embodiments, PGSU with an isocyanate-to-hydroxyl stoichiometric ratio between 1:0.25 and 1:1.25 demonstrates a zero-to-minimal inflammatory cell presence, minimal fibroplasia, and no fibrous encapsulation after 12 weeks of implantation. Additionally, in preferred embodiments, PGSU with an isocyanate-to-hydroxyl stoichiometric ratio in the range of 1:0.25 and 1:1.25 demonstrates zero cytotoxicity, zero acute systemic toxicity, zero irritation, zero subcutaneous implantation side effects, and zero intramuscular implantation side effects, per International Organization for Standardization (ISO) 10993 and USP Class VI test methods. Intramuscular implantation was carried out for 120 hours, while subcutaneous implantation was carried out for 7 days, and side effects assessed included clinical signs of toxicity, body weight, macroscopic evaluation for hemorrhaging, necrosis, discoloration, and infection, and fibrous encapsulation measurement.

In other embodiments, PGSU degradation products are anti-microbial, so that as the long-acting implantable breaks down, the local tissue environment has protection from infection on a long-term scale. In other embodiments, or in combination with the previous embodiment, unreacted PGSU low molecular weight oligomers and monomers are anti-microbial, such that upon swelling after implantation when these species are released as a bolus mass loss, the local tissue environment has protection from infection on a transient, short-term scale.

In other embodiments, a PGSU method of mixing and manufacture offers precision in urethane bond distribution, avoiding nitrogen clusters that may otherwise be present with poor mixing and that may cause unfavorable biological responses in poorly-mixed PGSU and poorly-mixed PGSU degradation products. The urethane bond nitrogen distribution has been confirmed to be uniform using infrared spectroscopy by interrogating different regions of PGSU films and also by generating micron-resolution heat maps of PGSU film surfaces.

The processes and compositions described herein may be included in any application that benefits from a biodegradable elastomer, such as, for example, cell scaffolds, textile filaments, microparticles, drug eluting stents, drug eluting textiles, 3D printing, medical devices, pharmaceuticals, drug products, combination device products, technical fabrics, food products, dermocosmetics, dental products, nutraceuticals, consumer devices, vehicle components, microtome sectioning, gaskets, tubing, sheets, insulation, seals, adhesives, containers, or cookware.

EXAMPLES

The invention is further described in the context of the following examples which are presented by way of illustration, not of limitation.

Example 1

PGS resins synthesized by a water-mediated process were compared to PGS resins synthesized by a non-water-mediated process. FIG. 1 shows the viscosity as a function of reaction time for the water-mediated process (10) compared to the non-water-mediated process (20).

PGS resins synthesized by a water-mediated process and PGS resins synthesized by a non-water-mediated process were characterized and analyzed. Four different batches of water-mediated PGS resins and four different batches of non-water-mediated PGS resins, having a weight-average molecular weight ($M_w$) over the range of about 10 kDa to about 50 kDa, were characterized. Table 1 shows the resulting data from the characterizations. Resins 1-4 were formed by a water-mediated process, and Resins 5-8 were formed by a non-water-mediated process.

TABLE 1

Water-mediated vs. Non-water-mediated PGS Sample Data

| Sample | $M_w$ by GPC (Da) | Zero-Shear Viscosity (Pa · s) | Polydispersity Index | Acid Number |
|---|---|---|---|---|
| Resin 1 | 13275 | 3.06 | 9.989 | 47 |
| Resin 2 | 22817 | 5.23 | 11.192 | 44 |
| Resin 3 | 27554 | 6.11 | 12.707 | 43 |

TABLE 1-continued

Water-mediated vs. Non-water-mediated PGS Sample Data

| Sample | $M_w$ by GPC (Da) | Zero-Shear Viscosity (Pa · s) | Polydispersity Index | Acid Number |
|---|---|---|---|---|
| Resin 4 | 47058 | 11.6 | 21.37 | 42 |
| Resin 5 | 11082 | 2.92 | 6.074 | 50 |
| Resin 6 | 21155 | 5.47 | 10.597 | 43 |
| Resin 7 | 27258 | 7.43 | 13.132 | 42 |
| Resin 8 | 50243 | 23.3 | 28.032 | 39 |

The data in Table 1 shows that the water-mediated PGS had a slightly lower zero-shear viscosity at the low molecular weight end and a zero-shear viscosity of about half at the high molecular weight end in comparison to the non-water-mediated PGS. Although the water-mediated PGS had a higher polydispersity index (PDI) at the low molecular weight end relative to the non-water-mediated PGS, the water-mediated PGS had a relatively lower PDI at the high molecular weight end. The measured acid number decreased more significantly with increasing molecular weight for the non-water-mediated PGS than the water-mediated PGS.

Figure 2:
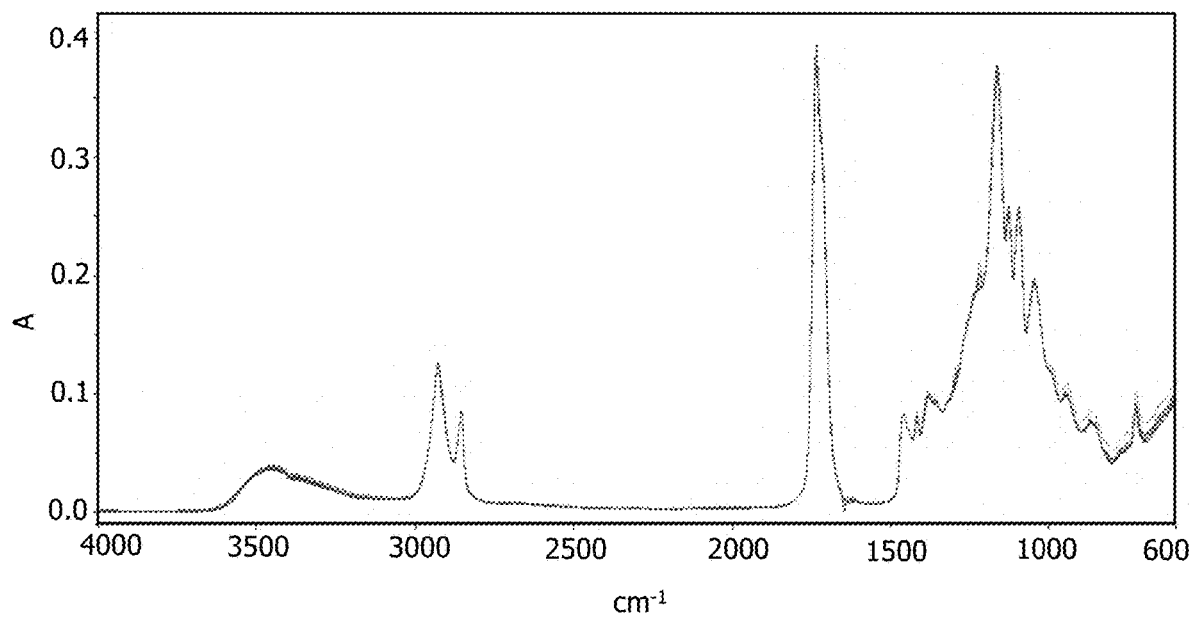
FIG. 2 shows Fourier-transform infrared (FTIR) spectra for a variety of PGS resin types.

FIG. 2 shows Fourier-transform infrared (FTIR) spectra for the eight resins. No dramatic differences were observed by FTIR between PGS resins, despite the crosslinked PGSU products exhibiting distinctly different physical properties, behaviors, reaction kinetics, and crosslinked network structure, as demonstrated in the following Examples. The small peak at about 1210 cm$^{-1}$ in FIG. 2 is attributed to crystallinity differences and has been shown to vary with resin temperature and storage and is not believed to be important for chemical functionality.

Figure 3:
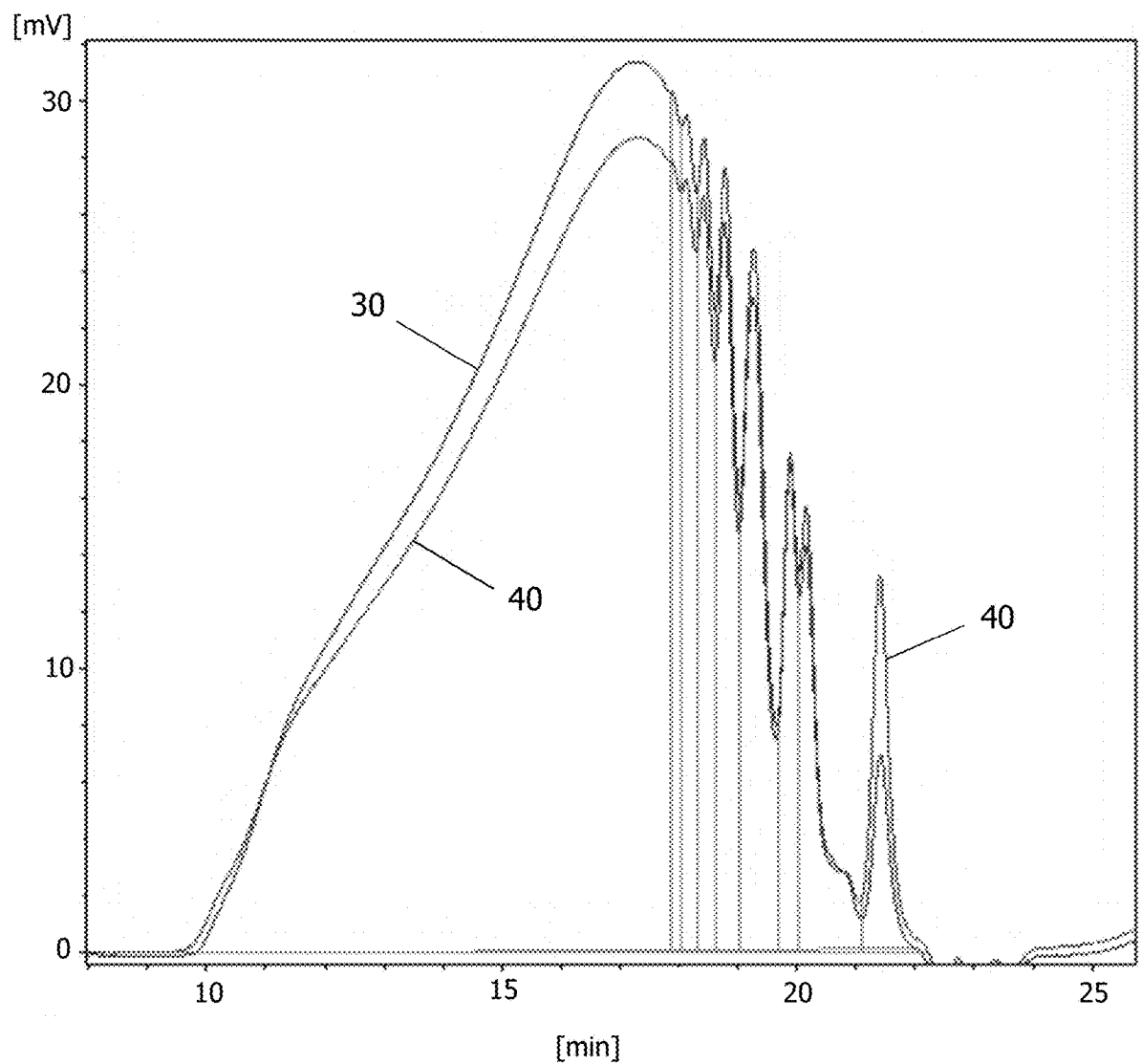
FIG. 3 shows GPC spectra for high-molecular-weight PGS resins formed by either a water-mediated process or a non-water-mediated process.

FIG. 3 shows the gel permeation chromatography (GPC) of PGS Resin 4 (30) and PGS Resin 8 (40). In the non-water-mediated resin, despite having a higher overall $M_w$, there is a lower proportion of mid $M_w$ fractions and higher proportion of low $M_w$ fractions. This is reflective of monomer, oligomer, and low $M_w$ fractions which do not get a chance to react in the non-water-mediated process. In the water-mediated process, these fractions can react due to the initial retardation caused by the addition of water. This results in a higher proportion of mid $M_w$ fractions and a lower proportion of low $M_w$ fractions. This shift in $M_w$ distribution results in more urethane crosslinks between mid $M_w$ fractions when the PGS resin is reacted with isocyanate to form PGSU. Having less low $M_w$ fractions available to participate in crosslinking leads to less chance the isocyanate will react with those small fugitive polymer chains, resulting in a PGSU crosslink network structure, three-dimensional conformation, and mesh size that display greater impermeability when the water-mediated process is used to synthesize PGS resin. Conversely, a non-water-mediated synthesized resin results in a PGSU crosslink network with higher permeability and less controlled drug release.

Example 2

Sixteen samples of PGSU films were formed by reacting each of Resin 1 through Resin 8 by combining and mixing each PGS resin with HDI at two different PGS:HDI mass ratios, 2.5:1 and 3.5:1, during film fabrication.

Figure 4:
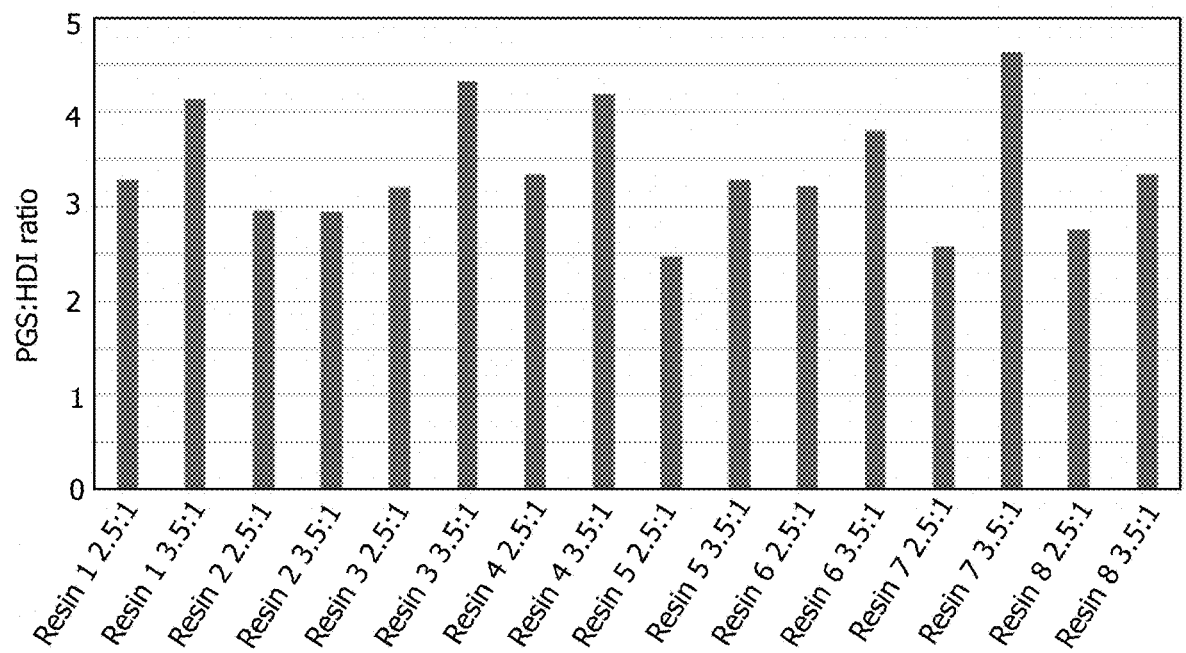
FIG. 4 shows PGSU crosslinking level as a PGS:HDI mass ratio based on FTIR spectra and a multiple linear regression model for PGSU made from a variety of PGS resin types.

The crosslinking of each PGSU film was estimated by FTIR spectroscopy and a multiple linear regression (MLR) model that used the integrated area of peaks highly correlated with crosslinking density. The resulting estimated crosslinking is shown in FIG. 4 as a PGS:HDI mass ratio. The PGS:HDI mass ratio is related to the crosslinking density, as shown in Example 5. PGS:HDI mass ratio can be converted to NCO:OH stoichiometric ratio using the hydroxyl value of the PGS resin and the equivalent weight of OH and equivalent weight of NCO. For reference, 3.5:1 PGS:HDI mass ratio films are less crosslinked than 2.5:1 PGS:HDI mass ratio films. FIG. 4 shows that different resins demonstrate different crosslinking behaviors, in some cases having lower crosslinking than would be expected if the PGS resin were Regenerez® RG-300 PGS resin, which the MLR model is based on and was trained with. For example, being estimated at 3:1 when the film was mixed at 2.5:1 is a lower-than-expected crosslinking. In some cases, PGS resins did not exhibit an increase in estimated PGS:HDI mass ratio despite an increase in the actual mass ratio from 3.5:1 to 2.5:1. In other cases, PGS resins exhibited a more dramatic increase in crosslinking between the mass ratios 3.5:1 and 2.5:1 than would be expected if using Regenerez® RG-300 PGS resin.

Figure 5:
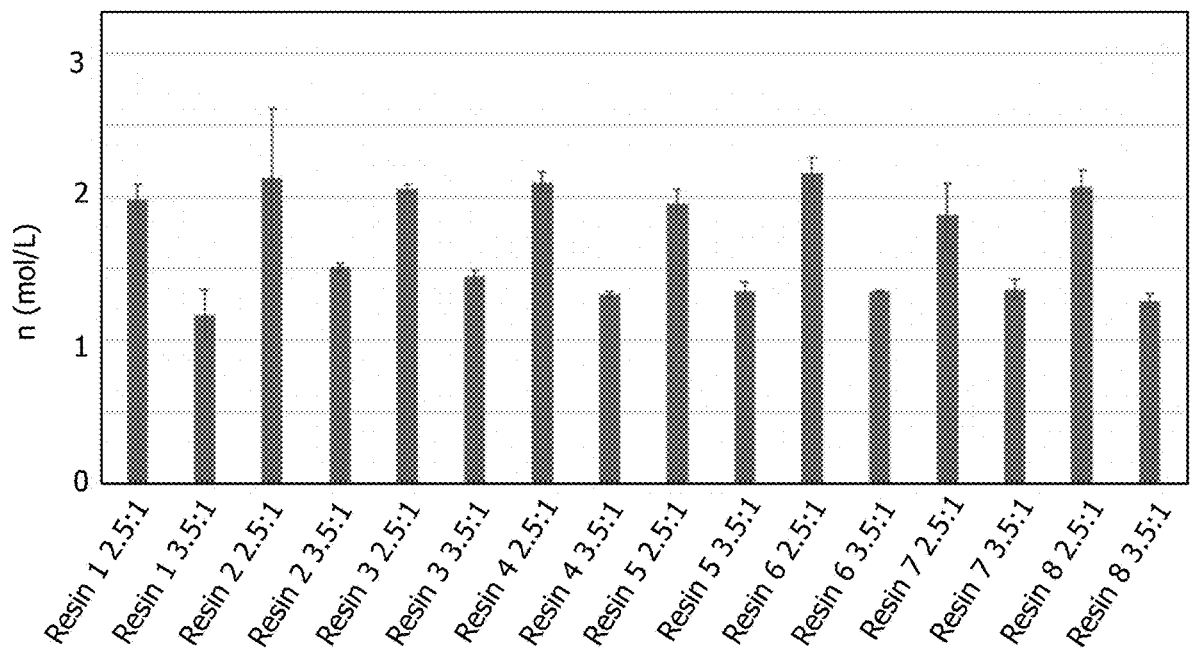
FIG. 5 shows PGSU crosslinking density as determined by Flory-Rehner swell testing for PGSU made from a variety of PGS resin types.

FIG. 5 shows crosslinking density, as determined by Flory-Rehner swell testing, of the sixteen PGSU films. Crosslinking in FIG. 5 is shown as moles per liter and describes the ability of a polymer network to swell. For reference, 3 mol/L films are more crosslinked than 2 mol/L films.

Example 3

Figure 6:
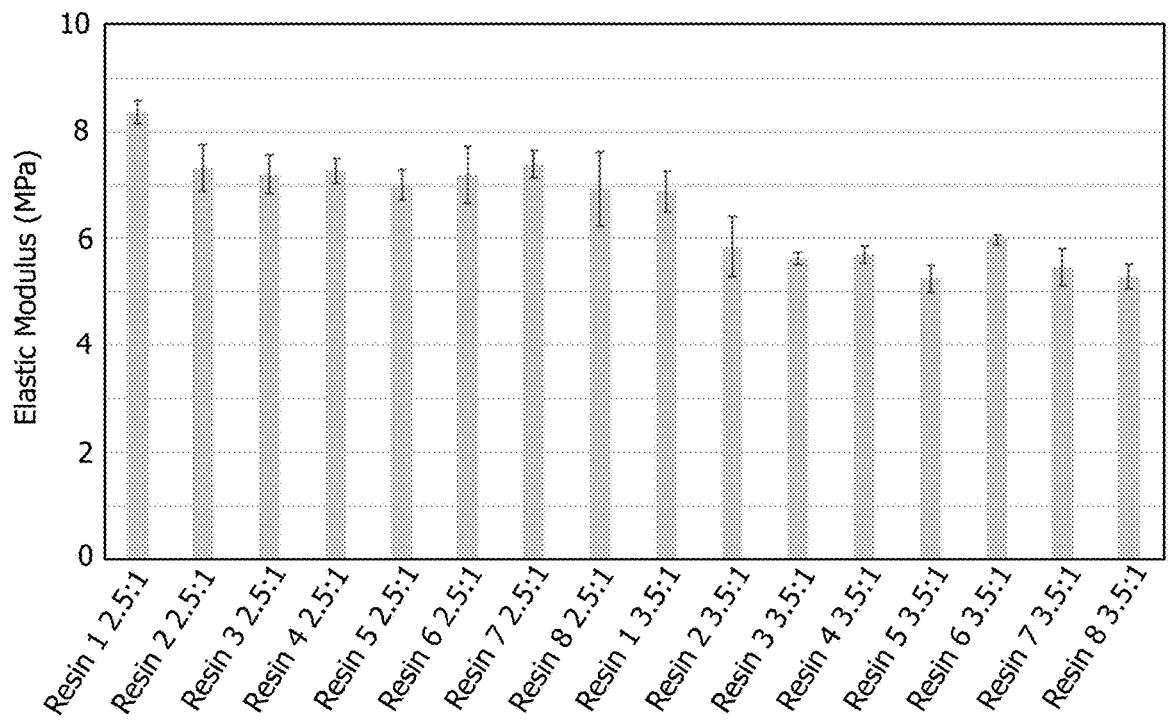
FIG. 6 shows elastic modulus for PGSU films made from a variety of PGS resin types.
Figure 7:
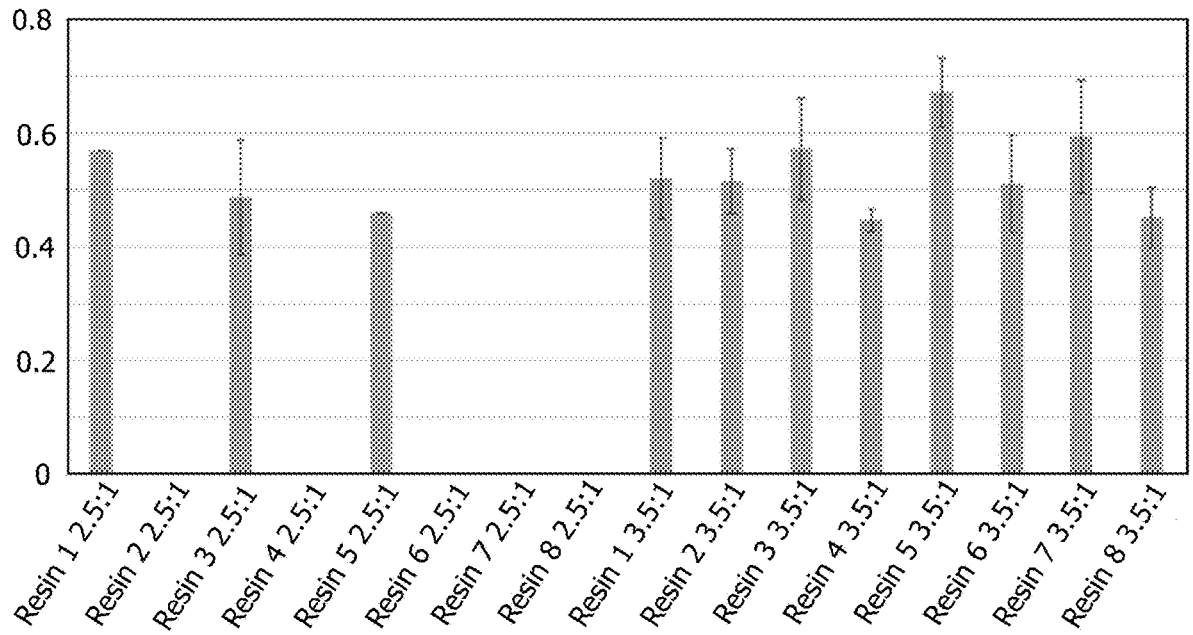
FIG. 7 shows strain at break for PGSU made from a variety of PGS resin types.

The sixteen samples of PGSU films were tested to determine elastic modulus, with the results being shown in FIG. 6, and strain at break, with the results being shown in FIG. 7, as determined by tensile testing. As shown in FIG. 7, PGSU films did not break in some cases such that no strain at break data could be collected. In these cases, increased PGSU crosslinking led to a tougher polymer that did not break, as opposed to a more brittle polymer behavior that might have been expected.

Example 4

Figure 8:
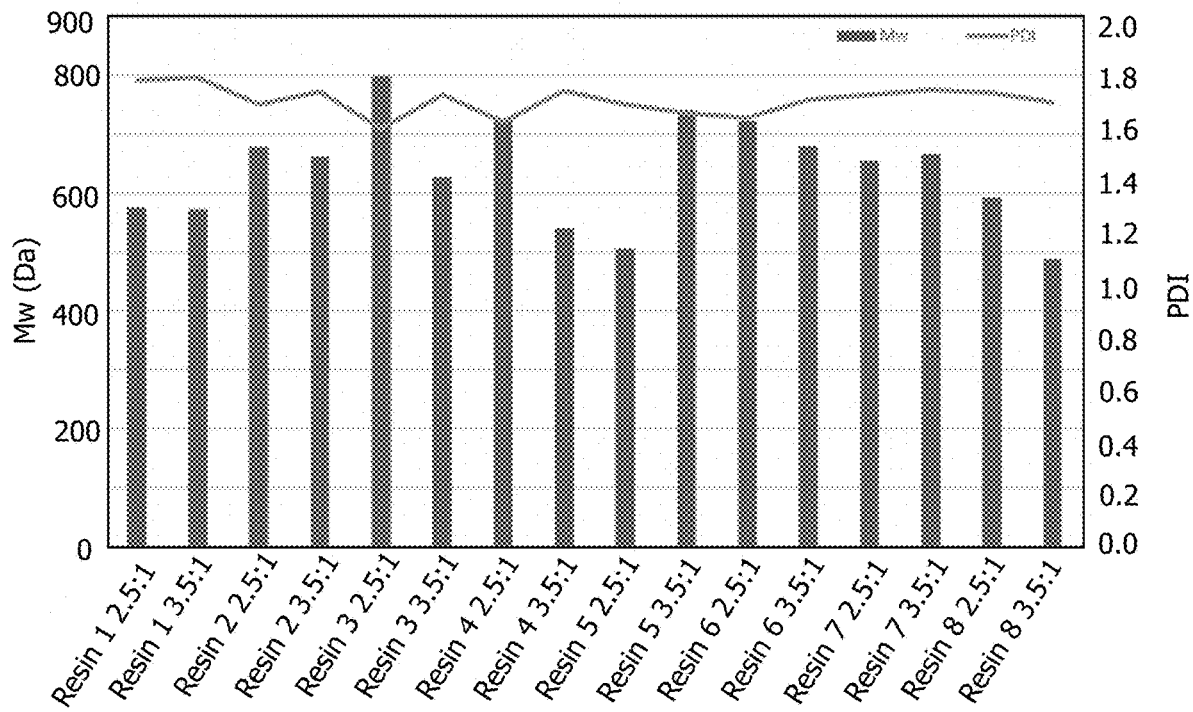
FIG. 8 shows weight-average molecular weight and polydispersity index of extractables collected from PGSU films from a variety of PGS resin types.
Figure 9:
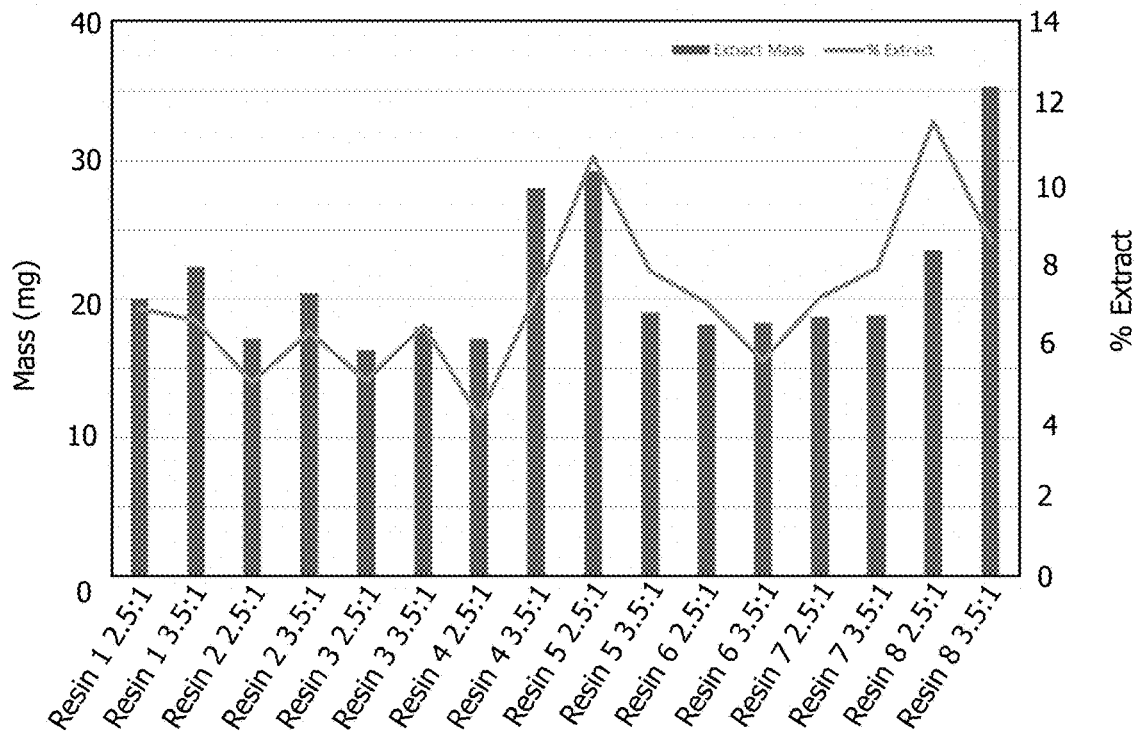
FIG. 9 shows mass and mass percentage of extractables collected from PGSU films, made from a variety of PGS resin types, based on the mass of the PGSU film.

Extractables from above the sixteen samples of PGSU films were collected and tested for weight-average molecular weight and polydispersity index, as determined by GPC, with the results being shown in FIG. 8. The $M_w$ species and PDI of the extractables was fairly similar across all samples, but the extractable $M_w$ tended to be slightly higher for intermediate PGS resin $M_w$ values. The proportion of extractable species varied across the different films' extractables, where films generated from water-mediated PGS resins tended to demonstrate less low $M_w$ fractions compared to films made from non-water-mediated PGS resins. The extracted mass and percentage of the mass extracted relative to the initial sample mass were also determined, with the results being shown in FIG. 9. The mass percentage of the extractables was more variable with PGS resin $M_w$ variation for the non-water-mediated PGSU samples.

Example 5

Figure 10:
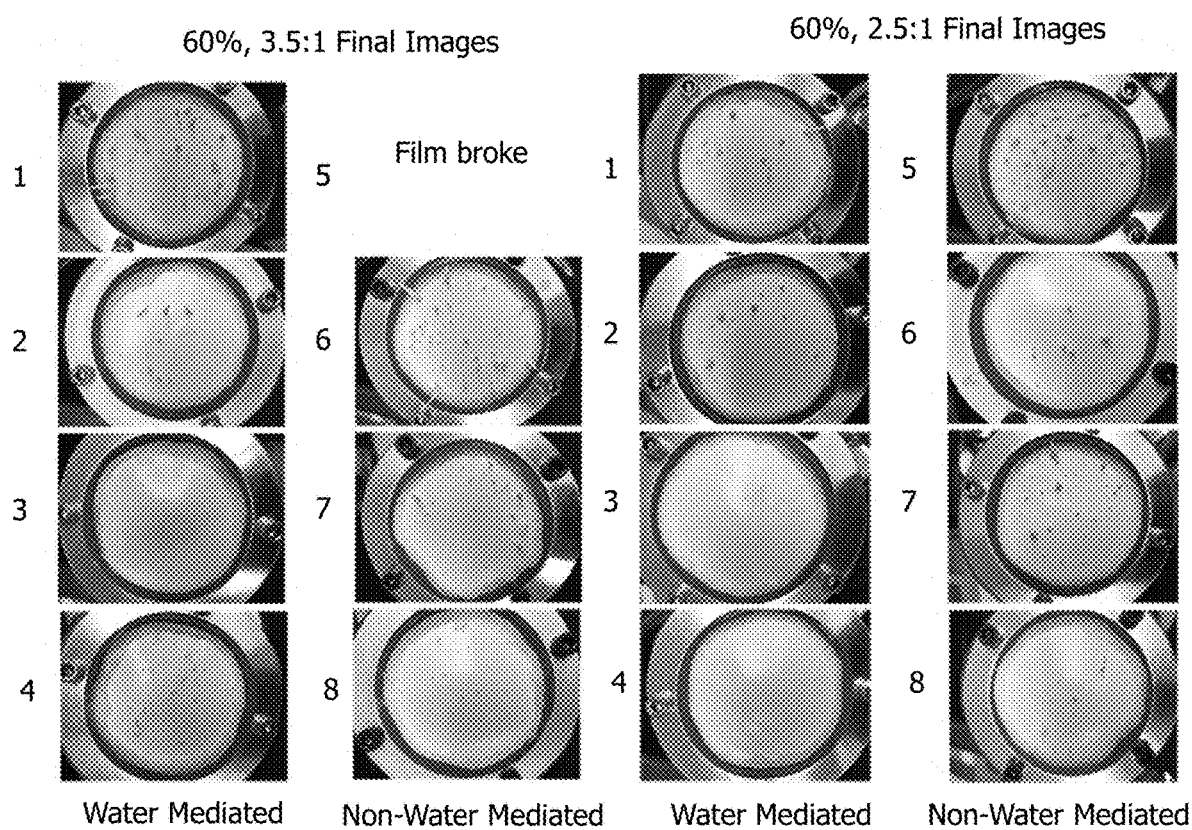
FIG. 10 shows bulk images of 60% w/w caffeine-loaded PGSU films after water exposure for different PGS resin molecular weights and different PGS:HDI ratios for PGSU films from a variety of PGS resin types.

Sixteen samples of PGSU films were formed as in Example 4, except in the presence of caffeine to form 60% w/w caffeine-loaded PGSU film samples. The sixteen samples of PGSU films were tested to determine water permeability and percolation, which directly relate to burst release and diffusion behaviors during drug release, with the results being shown in FIG. 10, FIG. 11, and Table 2. A modified water vapor transmission method from ASTM E96 was used, where a PGSU film barrier was placed over the top of a water-filled cup and inverted, so the water made direct contact with and could permeate through the PGSU film. High (>60% w/w) drug loadings of caffeine within PGSU films may exhibit some degree of percolation, due to high interconnectivity of caffeine drug particles spaced within the polymer matrix, creating interconnected channels and allowing for water infiltration. This was grossly visualized by the amount of caffeine precipitation the backside of the film. If water can permeate and percolate through the matrix, it will solubilize caffeine upon contact and carry the caffeine molecules along with it, until the water passes through the full film thickness and evaporates, leaving behind caffeine crystals. FIG. 10 images demonstrate that after two weeks 60% w/w loaded PGSU films experienced different degrees of permeation and percolation based on the resin and crosslinking density that was used. This can also be visualized more thoroughly using SEM, in FIG. 11, where cross-sections of films illustrate how far water was able to permeate and percolate in after two weeks, leaving behind voids where caffeine particles were solubilized and carried away. Arrows indicate direction of water infiltration. Water loss from the cup reservoir through the film over two weeks was quantified, with the results being shown below in Table 2.

TABLE 2

Water Loss through PGSU Films after 14 Days

| Resin | Loading (% w/w) | PGS:HDI Ratio | Initial Water (mL) | Final Water (mL) | Total Loss (%) |
|---|---|---|---|---|---|
| 1 | 60 | 2.5:1 | 50 | 43 | 14 |
|   |    | 3.5:1 | 50 | 18.5 | 63 |
| 2 | 60 | 2.5:1 | 50 | 26 | 48 |
|   |    | 3.5:1 | 50 | 10.5 | 79 |
| 3 | 60 | 2.5:1 | 50 | 48 | 4 |
|   |    | 3.5:1 | 50 | 48 | 4 |
| 4 | 60 | 2.5:1 | 50 | 48 | 4 |
|   |    | 3.5:1 | 50 | 35 | 30 |
| 5 | 60 | 2.5:1 | 50 | 11 | 78 |
|   |    | 3.5:1 | 50 | N/A | N/A |
| 6 | 60 | 2.5:1 | 50 | 45 | 10 |
|   |    | 3.5:1 | 50 | 13 | 74 |
| 7 | 60 | 2.5:1 | 50 | 44 | 12 |
|   |    | 3.5:1 | 50 | 15 | 70 |
| 8 | 60 | 2.5:1 | 50 | 47 | 6 |
|   |    | 3.5:1 | 50 | 46 | 8 |

Figure 11:
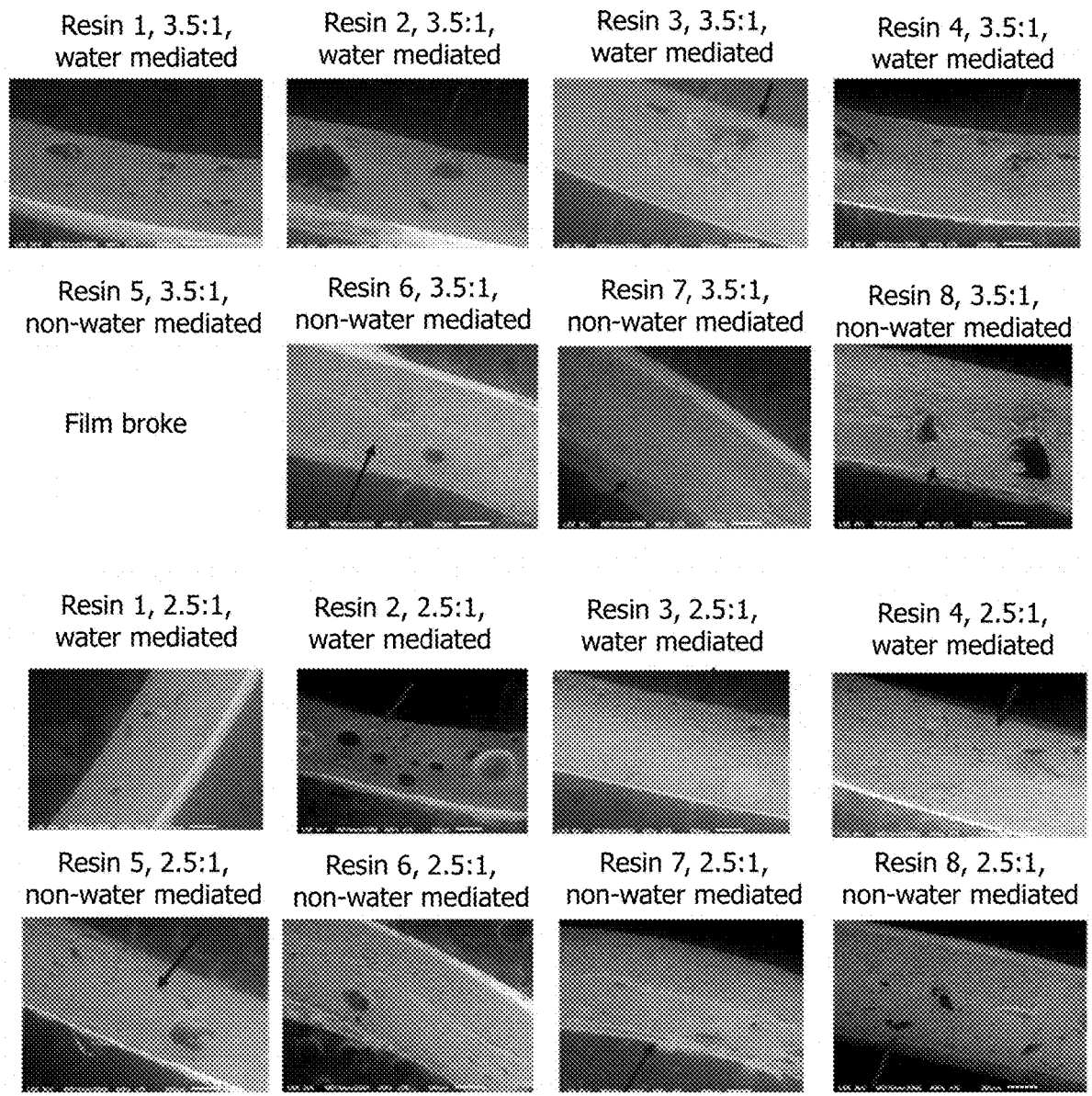
FIG. 11 shows cross-sectional scanning electron microscopy (SEM) images of 60% w/w caffeine-loaded PGSU films after water exposure for different PGS resin molecular weights and different PGS:HDI mass ratios for PGSU films from a variety of PGS resin types.

The data in Table 2 demonstrates a good correlation with the gross and SEM images of FIG. 10 and FIG. 11, respectively. Increasing PGSU crosslinking density from 3.5:1 to 2.5:1 reduced permeation and percolation of water through caffeine-loaded polymer films, for most, but not all, of the PGSU films made from different PGS resins.

Example 5

Figure 12:
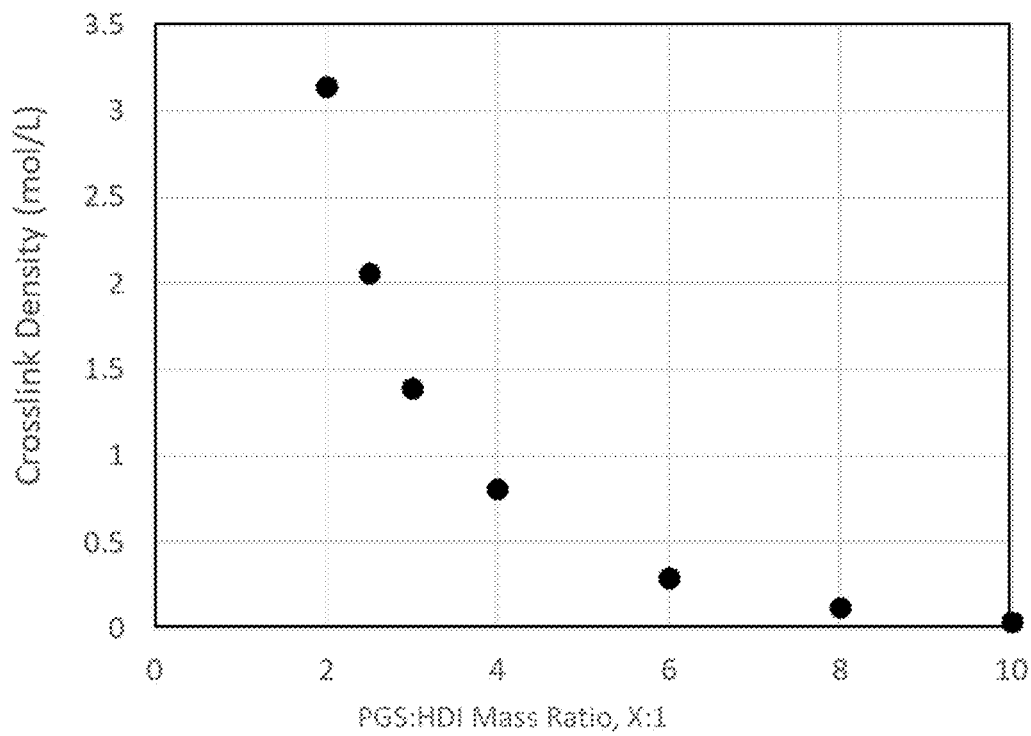
FIG. 12 shows how PGSU crosslinking density, as determined by an empirical swell test, relates to PGS:HDI mass ratio when using Regenerez® PGS resin (Secant Medical, Inc., Perkasie, PA).

Unloaded PGSU films were prepared by using a 60% w/w PGS solution in 1:1 (w/w) of acetone:propyl acetate. Regenerez® RG-300 PGS resin was used in this Example and all of the following Examples. Tin catalyst was added followed by HDI. Films were poured into molds and allowed to crosslink at room temperature for 24 hours, followed by a drying period at 40° C. for 6 days. The PGSU samples of different PGS:HDI mass ratios for unloaded (neat) formulations were synthesized and crosslink density was then measured. PGS:HDI mass ratios of 2:1 have higher crosslinking than ratios of 4:1 due to increased isocyanate in the formulation, but PGSU crosslinking does not follow a linear relationship with PGS:HDI mass ratio, as shown in FIG. 12.

Figure 13:
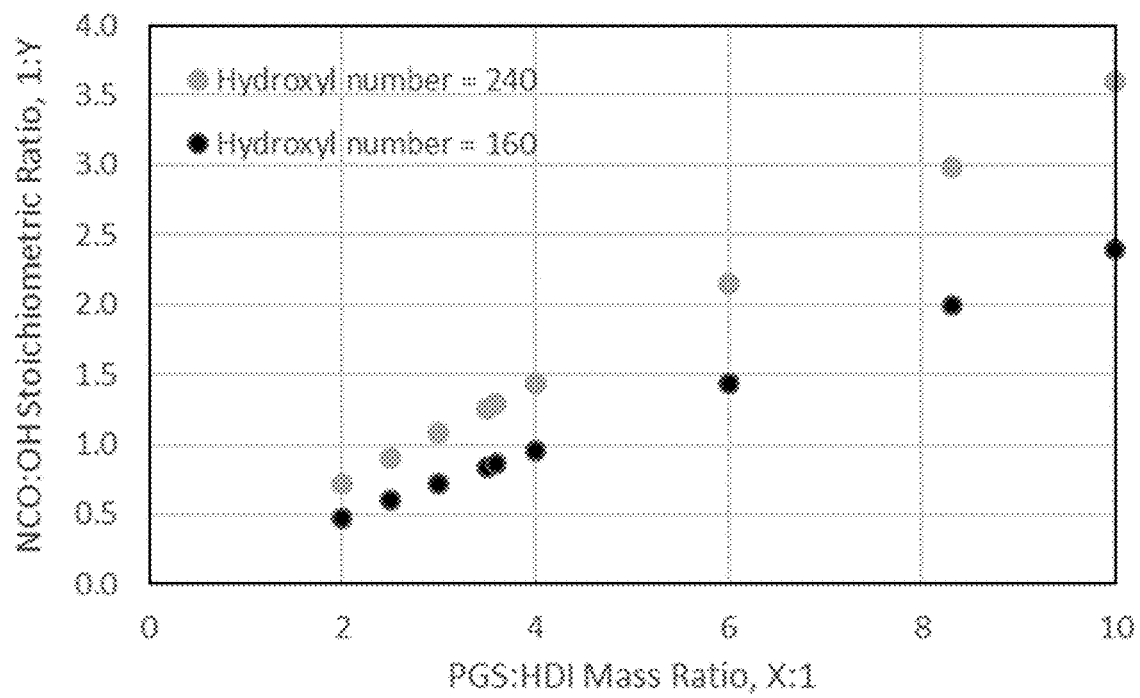
FIG. 13 shows how PGSU crosslinking density, as described by isocyanate-to-hydroxyl stoichiometric ratio, relates to PGS:HDI mass ratio when using Regenerez® PGS resin.

FIG. 13 shows how PGS:HDI mass ratio relates to isocyanate-to-hydroxyl stoichiometric ratio, for a PGS resin with a hydroxyl number between 160 and 240. For a given PGS:HDI mass ratio, a range of isocyanate-to-hydroxyl stoichiometric ratios could exist, depending on the hydroxyl number of the PGS resin. Gray data points demonstrate this relationship for a PGS resin with a hydroxyl number of 160, while black data points demonstrate this relationship for a PGS resin with a hydroxyl number of 240.

Figure 14:
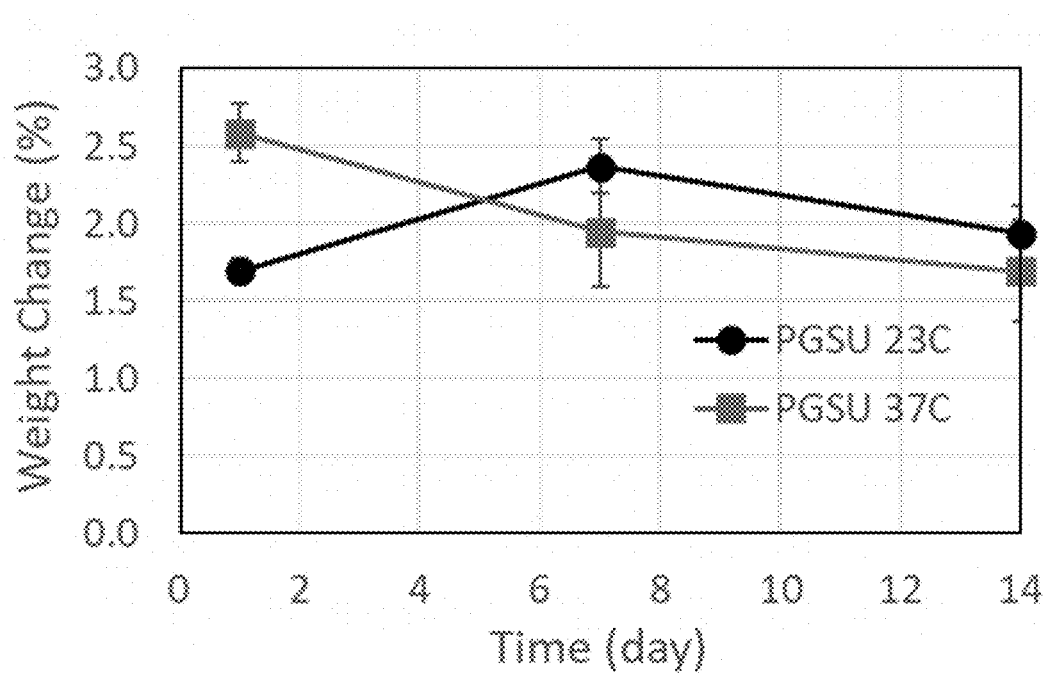
FIG. 14 shows swellability in water of unloaded PGSU films having a mass ratio of 3.6:1 PGS:HDI in a saline solution at 23° C. and 37° C., as measured by % weight change across 14 days, for PGSU made from Regenerez® PGS resin.

Swellability in saline solution of unloaded (neat) PGSU films having a PGS:HDI mass ratio 3.6:1 at 23° C. and 37° C., as measured by weight increase, remains below about 2.5% w/w across 14 days as shown in FIG. 14.

For a PGS resin with a hydroxyl number between 160 and 240, a PGS:HDI mass ratio of 3.6:1 results in an isocyanate-to-hydroxyl stoichiometric ratio between 1:0.86 and 1:1.3.

Example 7

Figure 15:
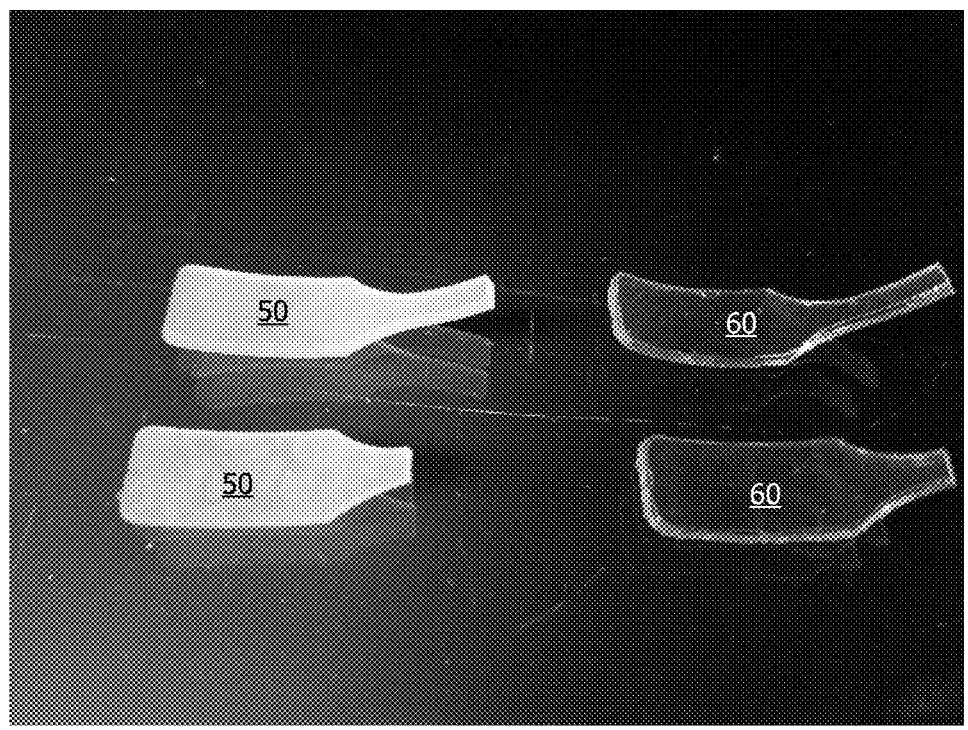
FIG. 15 shows thermoset PGSU products eight months after manufacture, for PGSU made from Regenerez® PGS resin.

PGSU samples (50) manufactured with a PGS:HDI mass ratio of 8.3:1 were initially clear, but became cloudy by three months after manufacture. The PGSU samples (50) remained cloudy through eight months after manufacture, as shown in FIG. 15. PGSU samples (60) manufactured with a PGS:HDI mass ratio of 3.6:1 were initially clear and remained clear through three months after manufacture. The PGSU samples (60) remained clear through eight months after manufacture, as shown in FIG. 15.

The lack of clarity seen in the 8.3:1 PGS:HDI mass ratio polymer may be an indicator of instability and thus poor shelf life. The instability may be in the form of polymer chain reorientation, migration, or blooming. Clouding, hazing, and blooming may impact product quality, shelf life, and controlled release behavior.

For a PGS resin with a hydroxyl number between 160 and 240, a PGS:HDI mass ratio of 3.6:1 results in an isocyanate-to-hydroxyl stoichiometric ratio between 1:0.86 and 1:1.3, while a PGS:HDI mass ratio of 8.3:1 results in an isocyanate-to-hydroxyl stoichiometric ratio between 1:2 to 1:3. Accordingly, this data shows that polymer clouding occurs at isocyanate-to-hydroxyl stoichiometric ratios below 1:2, such as, for example, 1:3 or 1:4.

Example 8

Seven samples of API-loaded PGSU were formed with caffeine as the API to measure drug release from PGSU during in vivo pharmacokinetic testing using a rat preclinical model with dorsal subcutaneous implantation. The PGSU was formed from PGS resin having a weight-average molecular weight of about 18,000 Da and a polydispersity index of about 9. As shown in Table 3 below, six of the samples had a low crosslinking density in the range of 0.51 to 0.89 mol/L and either a lower initial loadings of caffeine in the range of 18.2% to 20.9% w/w or a higher initial loading of caffeine in the range of 24.8% to 25.3% w/w. Sample R7 had a high crosslinking density of 2.75 mol/L and an intermediate loading of caffeine.

Each sample was implanted by dorsal subcutaneous implantation in a Wistar Han rat model, and caffeine release from each sample in vivo was monitored over about 90 days. FIG. 16 shows the caffeine concentration measured in plasma, indicating sustained release of caffeine over the 3-month time period for most samples. The high crosslinking sample had a significantly slower release rate than the low crosslinking samples. The residual loading was measured at the end of the study, with the measured values being shown in Table 3.

TABLE 3

PGSU-caffeine in vivo Sample Data

| Sample | Crosslinking Density (mol/L) | Initial Loading (% w/w) | Residual Loading (% w/w) |
|---|---|---|---|
| R1 | 0.85 | 20.9 | 0.7 |
| R2 | 0.86 | 18.2 | 0.0 |
| R3 | 0.89 | 18.3 | N/A |
| R4 | 0.51 | 19.6 | N/A |
| R5 | 0.65 | 24.8 | 0.0 |
| R6 | 0.64 | 25.3 | 0.0 |
| R7 | 2.75 | 23.7 | 18.9 |

Release rate was near zero-order across different loadings and different crosslinking levels. Burst release was particularly minimal in highly crosslinked PGSU rods, with only a 4-fold difference in concentration between $C_{max}$ and $C_{steady}$ for R7. PGSU rods were fabricated with caffeine loading range from about 15% to 25% w/w. Based on residual caffeine loading in explanted rods, only about 20% of the caffeine payload was released over 3 months for the highly crosslinked PGSU rod in R, and it can be extrapolated that the implant may have continued releasing caffeine for 9 additional months, totaling 12 months of release.

Example 9

Eight samples of API-loaded PGSU rods were formed with caffeine as the API at loading range from about 15% to about 25% w/w. Samples were stored either three months under accelerated aging conditions or six months under real time aging conditions. As shown in Table 4 below, two of the real-time aged samples had low initial loadings of caffeine, two of the real-time aged samples had high initial loadings of caffeine, two of the accelerated aged samples had low initial loadings of caffeine, and two of the accelerated aged samples had high initial loadings of caffeine. Most of the samples had low crosslinking levels, but F4 and F8 had high crosslinking levels.

TABLE 4

PGSU-caffeine in vitro Sample Data

| Sample | Shelf Life Storage | Initial Loading (% w/w) |
|---|---|---|
| F1 | 6 months, real time aging | 14.6 |
| F2 | 6 months, real time aging | 14.9 |
| F3 | 6 months, real time aging | 24.8 |
| F4 | 6 months, real time aging | 19.3 |
| F5 | 3 months, accelerated aging | 12.1 |
| F6 | 3 months, accelerated aging | 15.7 |
| F7 | 3 months, accelerated aging | 24.6 |
| F8 | 3 months, accelerated aging | 20.5 |

Each sample was placed in a flow-through cell USP IV apparatus with flow of 0.1 M phosphate-buffered saline (PBS) at a pH of 7.4 at 37° C. and a flow rate of 8 mL/min, and the cumulative release of caffeine from each sample in vitro was monitored over about 55 days. FIG. 17 shows the cumulative amount of caffeine in the PBS, indicating sustained release of caffeine over the 2-month time period for all samples. The high crosslinking samples had significantly slower release rates.

Example 10

Figure 18:
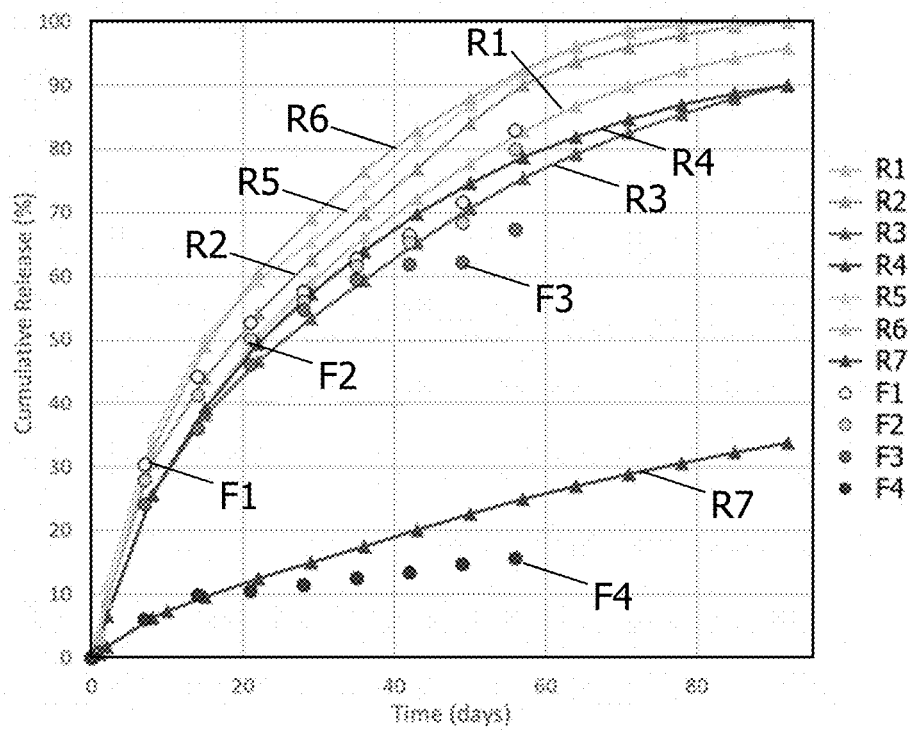
FIG. 18 shows in vitro-in vivo overlays for cumulative release for implantable PGSU rod products with 15% to 25% w/w API loadings at different crosslinking densities, for PGSU made from Regenerez® PGS resin.

The percentage of cumulative release of caffeine was plotted for both the in vivo and the in vitro experiments of Examples 8 and 9. The results are shown in FIG. 18. Both the in vivo and the in vitro experiments had similar release curves for the low crosslinking samples, regardless of the API loading percentage.

Figure 19:
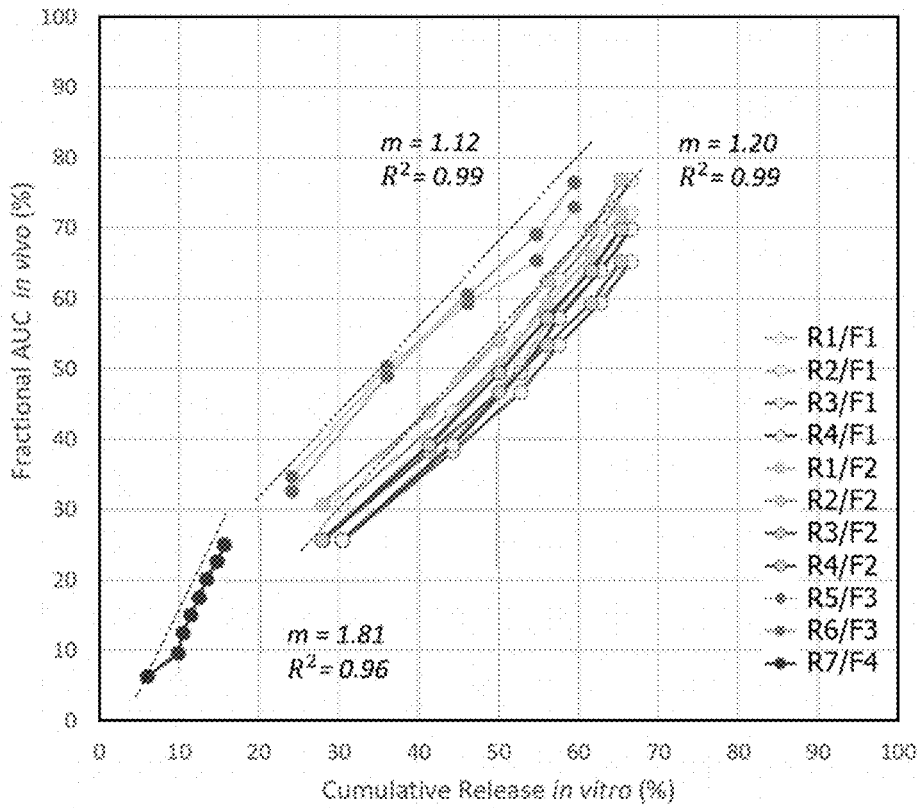
FIG. 19 shows in vitro-in vivo correlations for cumulative release for implantable PGSU rod products with 15% to 25% w/w API loadings at different crosslinking densities, for PGSU made from Regenerez® PGS resin.

To determine the correlation between the in vivo and the in vitro results, pairs of in vivo and in vitro samples with similar relative API loadings and similar relative crosslinking levels were matched up and each data point in FIG. 8 represents the fractional area under the curve (AUC) for the in vivo sample and the cumulative release for the in vitro sample at the same time from the start of each experiment. As shown by the line fits in FIG. 19, correlation shows agreement between methods and grouping of higher crosslinked PGSU compared to lower crosslinked PGSU. Different drug loadings did not dramatically affect in vivo-in vitro correlation linearity or slope.

Figure 20:
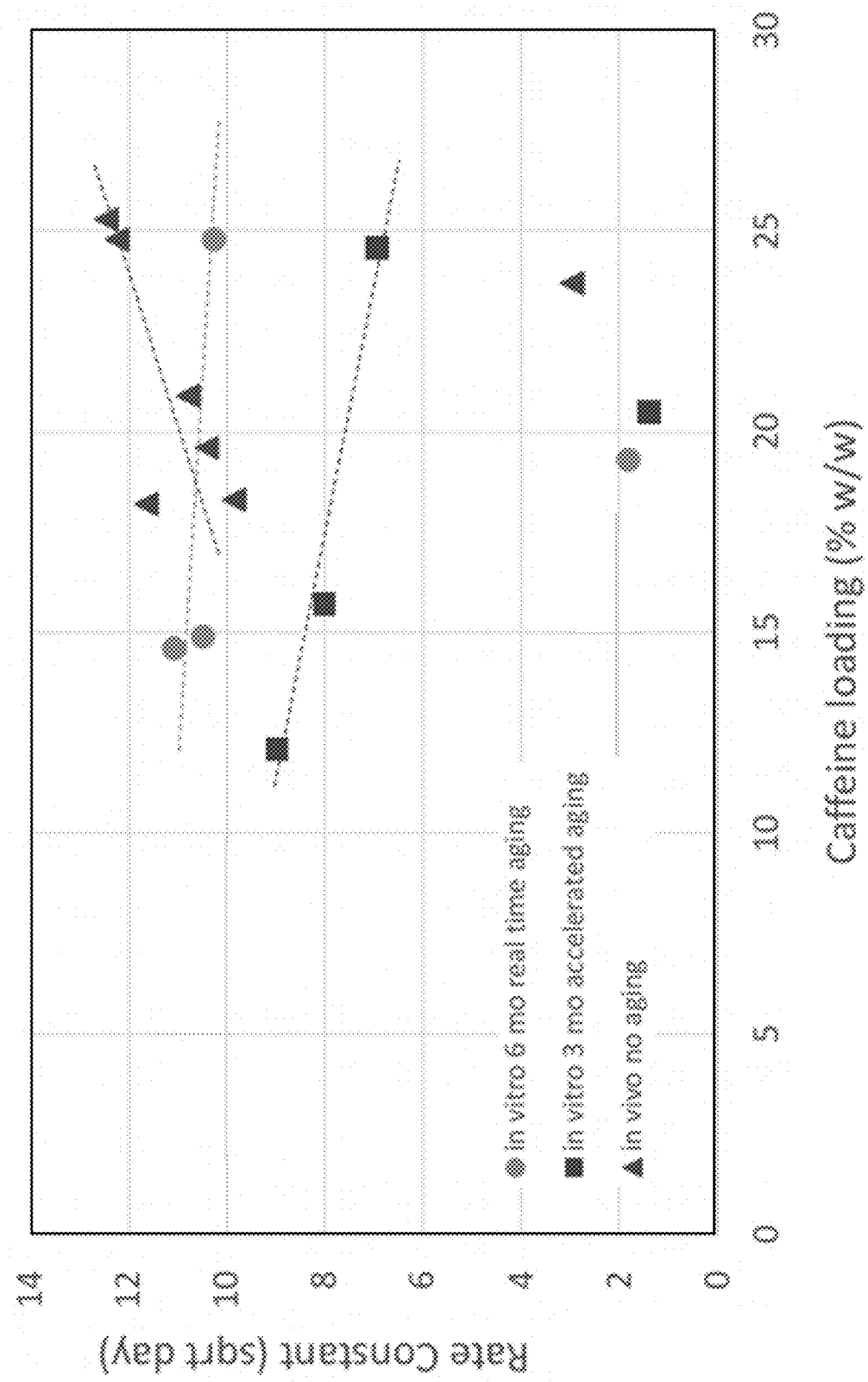
FIG. 20 shows the observed near zero-order release rate constant relative to the initial caffeine loading for the in vivo and in vitro results of FIG. 16 and FIG. 17, for PGSU made from Regenerez® PGS resin.

The release rates for the seven samples of Example 8 and the eight samples of Example 9 were calculated based on the release data. FIG. 20 shows the release rate plotted as a function of the initial caffeine loading indicating a zero-order or near zero-order release rate substantially independent of API loading across the tested API loadings. During both in vitro and in vivo caffeine release from PGSU, the rate constant remains nearly the same across drug loadings and appears to be independent of drug loading. PGSU's surface erosion properties allow for this, compared to bulk-eroding or non-degradable polymers where the rate constant dramatically increases as drug loading is increased. Higher crosslinked PGSU can be grouped separately from lower crosslinked PGSU and exhibited a much lower rate constant of about 2 day$^{1/2}$, while lower crosslinked PGSU exhibited a rate constant of about 8 to about 12 day$^{1/2}$. The lower the rate constant, the longer a drug-releasing implant can provide therapy. Achieving long-lasting implants are high loadings has been prohibitive for bulk-eroding and non-degradable polymers, but surface-eroding PGSU overcomes this limitation.

Figure 21A:
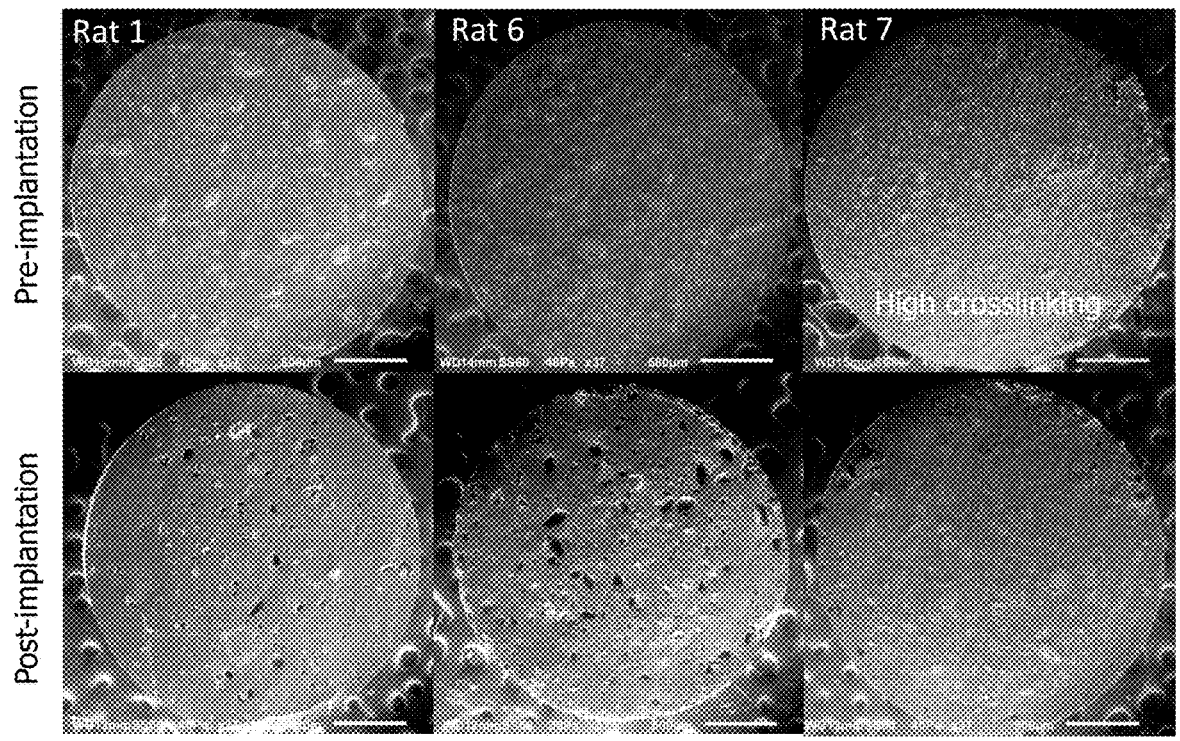
FIG. 21A shows cross-sectional images of caffeine-loaded PGSU rods before and after implantation in rats, for PGSU made from Regenerez® PGS resin.
Figure 21B:
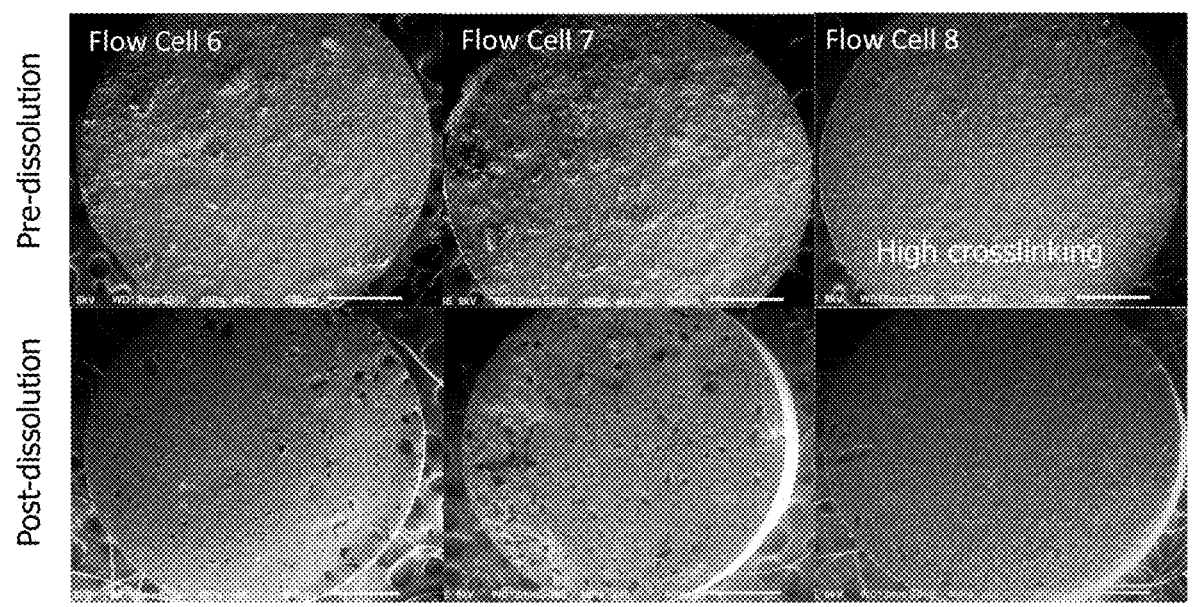
FIG. 21B shows cross-sectional images of caffeine-loaded PGSU rods before and after dissolution testing, for PGSU made from Regenerez® PGS resin.

Caffeine-loaded PGSU demonstrates diffusion-driven drug release when PGSU crosslinking is low, but at high PGSU crosslinking, diffusion is curtailed and drug release is driven truly by surface erosion. Cross-sectional images shown in FIG. 21A illustrate rods before and after implantation in rats, and cross-sectional images in FIG. 21B illustrate rods before and after dissolution testing. In cases where drug diffused out of the matrix, voids were left behind where pockets of caffeine used to be present, in lower crosslinked PGSU. In higher crosslinked PGSU, no voids were present, and water or bodily fluids were not able to penetrate into the matrix and cause drug diffusion back out of the matrix. By increasing PGSU crosslinking, diffusion and burst release can be minimized or eliminated entirely.

Example 11

Figure 22:
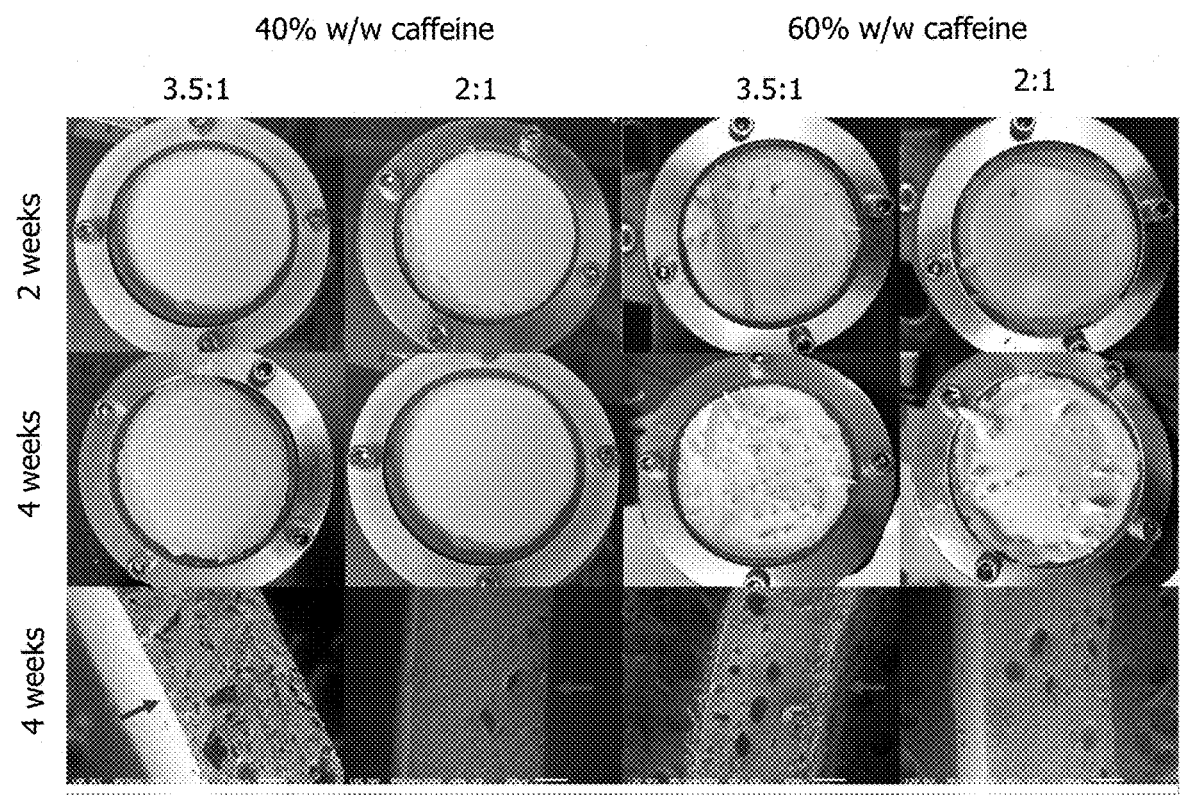
FIG. 22 shows water permeation and percolation of 40% w/w caffeine-loaded PGSU films and 60% w/w caffeine-loaded PGSU films, for PGSU made from Regenerez® PGS resin.

Loaded PGSU films were prepared by using a 60% w/w PGS solution in 1:1 (w/w) of acetone:propyl acetate. Tin catalyst was added, followed by caffeine as a model compound, followed by HDI. Films were poured into molds and allowed to crosslink at room temperature for 24 hours, followed by a drying period at 40° C. for 6 days. Four caffeine-loaded PGSU films were formed and tested for water permeability using a modified water vapor transmission method from ASTM E96, where a film barrier was placed over the top of a water-filled cup and inverted, so the water made direct contact with and could permeate through the PGSU film. Two films had 40% w/w caffeine loading and the other two had 60% w/w loading. One each of the 40% and 60% loadings was formed with a 3.5:1 PGS:HDI mass ratio and the others were formed with a 2:1 PGS:HDI mass ratio. Higher drug loadings of caffeine within PGSU films led to increased percolation, due to increased interconnectivity of caffeine drug particles spaced within the polymer matrix, creating interconnected channels and allowing for easier water infiltration. This can be grossly visualized by the amount of caffeine precipitation the backside of the film. If water can permeate and percolate through the matrix, it will solubilize caffeine upon contact and carry the caffeine molecules along with it, until the water passes through the full film thickness and evaporates, leaving behind caffeine crystals. FIG. 22 shows that 60% w/w loaded PGSU films experienced greater permeation and percolation than 40% w/w loaded films. FIG. 22 also includes SEM images of cross-sections of films that illustrate how far water was able to permeate and percolate in, leaving behind voids where caffeine particles were solubilized and carried away. Arrows indicate direction of water infiltration. Increasing PGSU crosslink density from 3.5:1 to 2:1 reduced permeation and percolation of water through caffeine-loaded polymer films, both for 40% w/w and 60% w/w loaded films.

For a PGS resin with a hydroxyl number between 160 and 240, a PGS:HDI mass ratio of 2:1 results in an isocyanate-to-hydroxyl stoichiometric ratio between 1:0.48 and 1:0.72, 2.5:1 results in an isocyanate-to-hydroxyl stoichiometric ratio between 1:0.6 and 1:0.9, 3:1 results in an isocyanate-to-hydroxyl stoichiometric ratio between 1:0.72 and 1:1.08, and 3.5:1 results in an isocyanate-to-hydroxyl stoichiometric ratio between 1:0.84 and 1:1.26.

Example 12

PGSU rods were loaded with different types of model drug substances including barium sulfate (20% w/w), USP grade barium sulfate (20% w/w), and caffeine (20% and 30% w/w), but still exhibited a high flexibility and tight bend radius of about 1 to 2 mm when folded 180° comparable to neat (unloaded) PGSU rods.

Example 13

Figure 23:
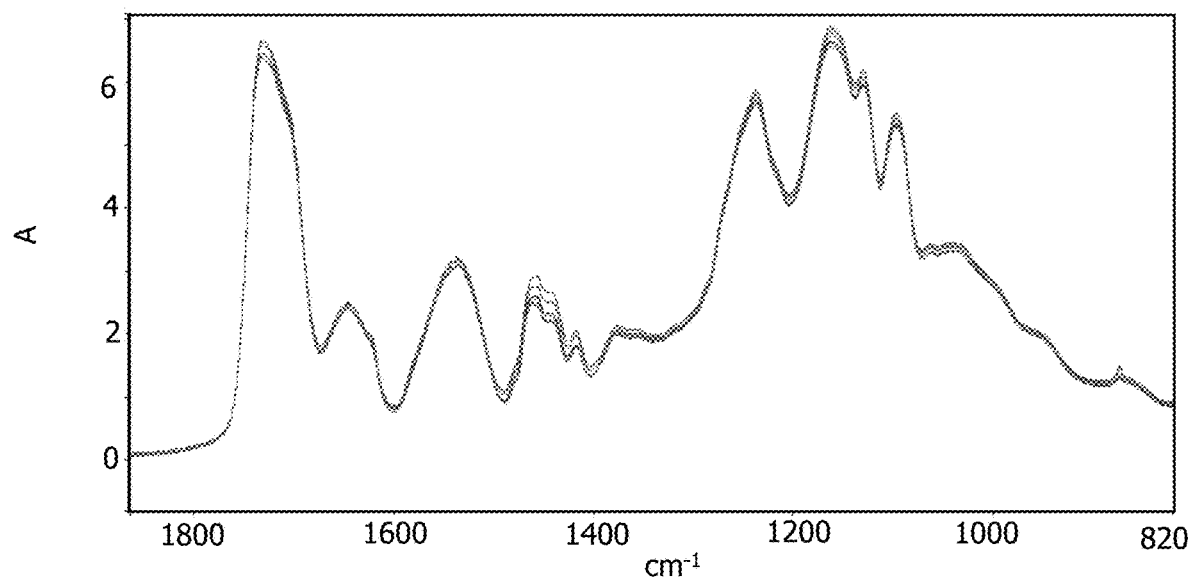
FIG. 23 shows FTIR spectra of homogeneously mixed PGSU achieved by high shear mixing, before and after gamma sterilization, for PGSU made from Regenerez® PGS resin.
Figure 24:
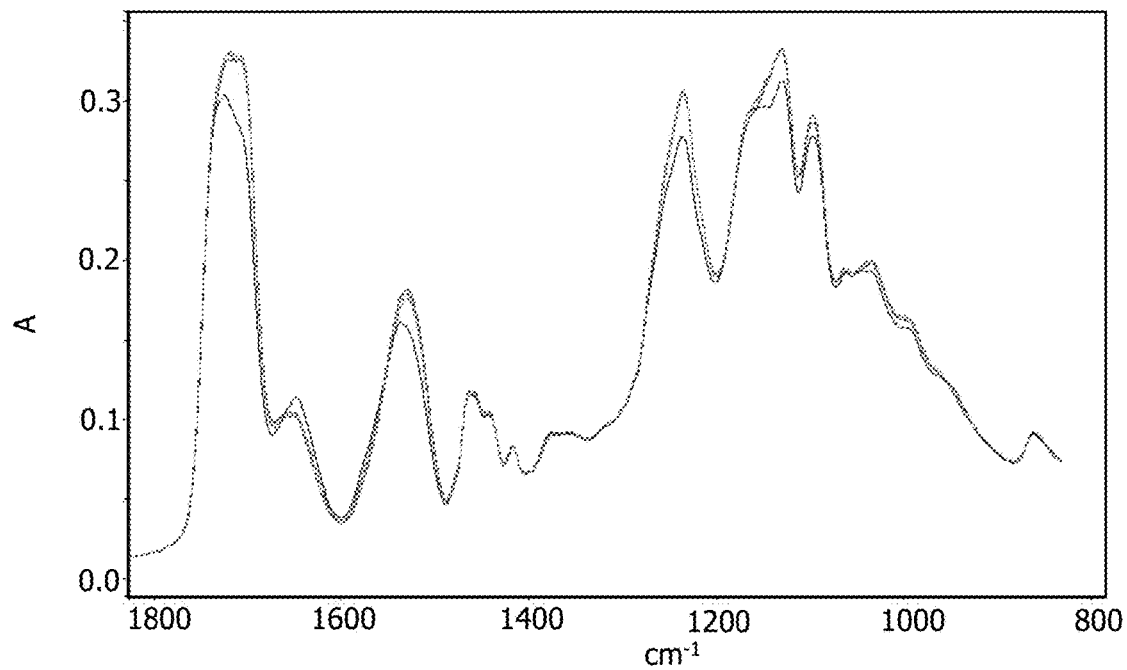
FIG. 24 shows FTIR spectra of poorly mixed PGSU resulting from low shear mixing, for PGSU made from Regenerez® PGS resin.

Unloaded PGSU sheets with PGS:HDI mass ratios of 2:1, 2.5:1, 3:1, 3.5:1 and 4:1 were interrogated using FTIR to assess the spatial homogeneity of crosslinking density and relatedly uniformity of mixing. PGSU films were prepared by using a 60% w/w PGS solution in 1:1 (w/w) of acetone:propyl acetate. Tin catalyst was added followed by HDI. High shear mixing techniques were employed at component addition steps. Films were poured into molds and allowed to crosslink at room temperature for 24 hours, followed by a drying period at 40 C for 6 days. No differences in FTIR peaks associated with urethane or ester crosslinking bonds were observed across five distinct spatial locations on PGSU films, as shown in FIG. 23 for 2:1 PGS:HDI mass ratio films in the region between 1800 and 800 cm$^{-1}$. Additionally, no differences in spectra were observed in the hydroxyl region between 3500 and 3100 cm$^{-1}$. The region between 1475 and 1400 cm$^{-1}$ are C—H$_2$ alkane bends and C—H alkene in-plane bends that are not associated with urethane bonds in PGSU crosslinking. Further, no differences in any FTIR peaks were observed between unsterilized and gamma-irradiated sterile PGSU sheets. However, film fabrication methods that did not incorporate high shear mixing techniques but otherwise were identical failed to achieve mixing uniformity and spatial homogeneity of crosslinking density, as evidenced by highly variable FTIR peaks associated with urethane and ester crosslinking bonds, as shown in FIG. 24 for 2:1 PGS:HDI mass ratio films in the region between 1800 and 800 cm$^{-1}$. It becomes especially challenging to achieve good mixing at high crosslinking where large volumes of isocyanate are used, such as 2:1 PGS:HDI mass ratio, due to miscibility and viscosity issues. FIG. 23 and FIG. 24 show the importance of high shear mixing, particularly at 2:1 PGS:HDI mass ratio.

For a PGS resin with a hydroxyl number between 160 and 240, a PGS:HDI mass ratio of 2:1 results in an isocyanate-to-hydroxyl stoichiometric ratio between 1:0.48 and 1:0.72, 2.5:1 results in an isocyanate-to-hydroxyl stoichiometric ratio between 1:0.6 and 1:0.9, 3:1 results in an isocyanate-to-hydroxyl stoichiometric ratio between 1:0.72 and 1:1.08, 3.5:1 results in an isocyanate-to-hydroxyl stoichiometric ratio between 1:0.84 and 1:1.26, and 4:1 results in an isocyanate-to-hydroxyl stoichiometric ratio between 1:0.96 and 1:1.44.

Example 14

Figure 25:
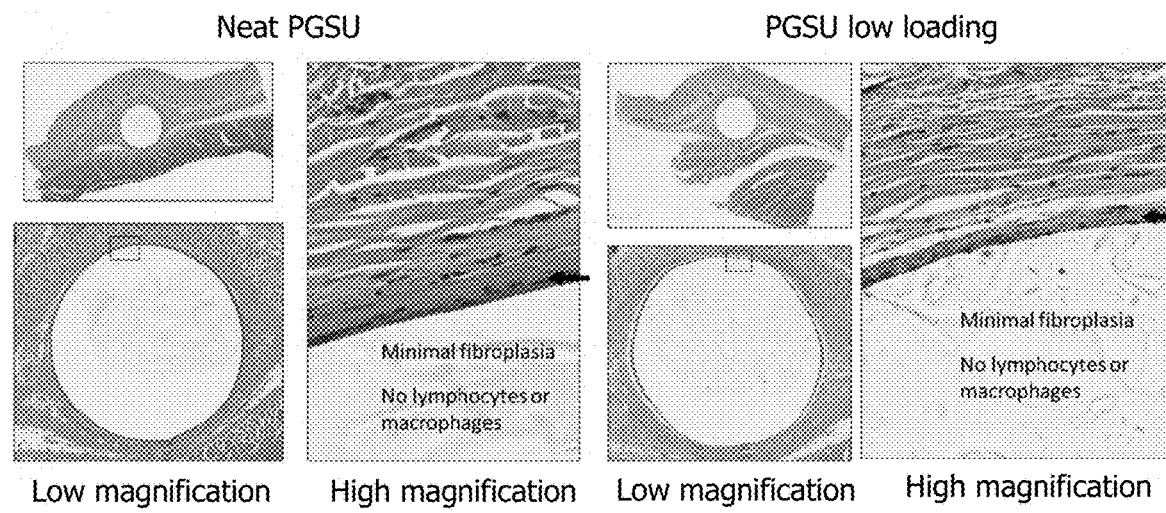
FIG. 25 shows histology at the three month timepoint of explanted PGSU rod products, initially with and without 15% to 25% w/w API loading, and the surrounding subcutaneous tissue and underlying muscle, for biocompatibility assessment, for PGSU made from Regenerez® PGS resin.

The neat (unloaded) PGSU and (loaded) PGSU with caffeine-loading of Example 8 were observed to demonstrate biocompatibility after 3 months of implantation in rats, with minimal fibroplasia, no fibrous encapsulation, and no lymphocyte or macrophage infiltration upon histological inspection, indicating no adverse response to the material, its leachables, or its degradation byproducts as shown in FIG. 25. Additionally, following ISO 10993 testing for cytotoxicity, acute systemic toxicity, irritation, and implantation, unloaded PGSU sheets with a 3.6:1 PGS:HDI mass ratio passed all biocompatibility tests with scores of 0 across all samples and all animals, indicating no adverse response to the material or its extractables and leachables. PGS-based biomaterials have breakdown products less acidic than other polyesters such as PLGA, PGA, or PLA, which reduces the inflammatory response, toxicity, delayed healing, and negative impact on cells resulting from acidic pH. Further, more highly crosslinked PGSU may incite less acute inflammation, chronic inflammation, and fibrosis due to fewer exposed chemical functional groups at the cell-interfacing surface that may aggravate or activate immune cells.

For a PGS resin with a hydroxyl number between 160 and 240, a PGS:HDI mass ratio of 3.6:1 results in an isocyanate-to-hydroxyl stoichiometric ratio between 1:0.86 and 1:1.3.

Example 15

Figure 26:
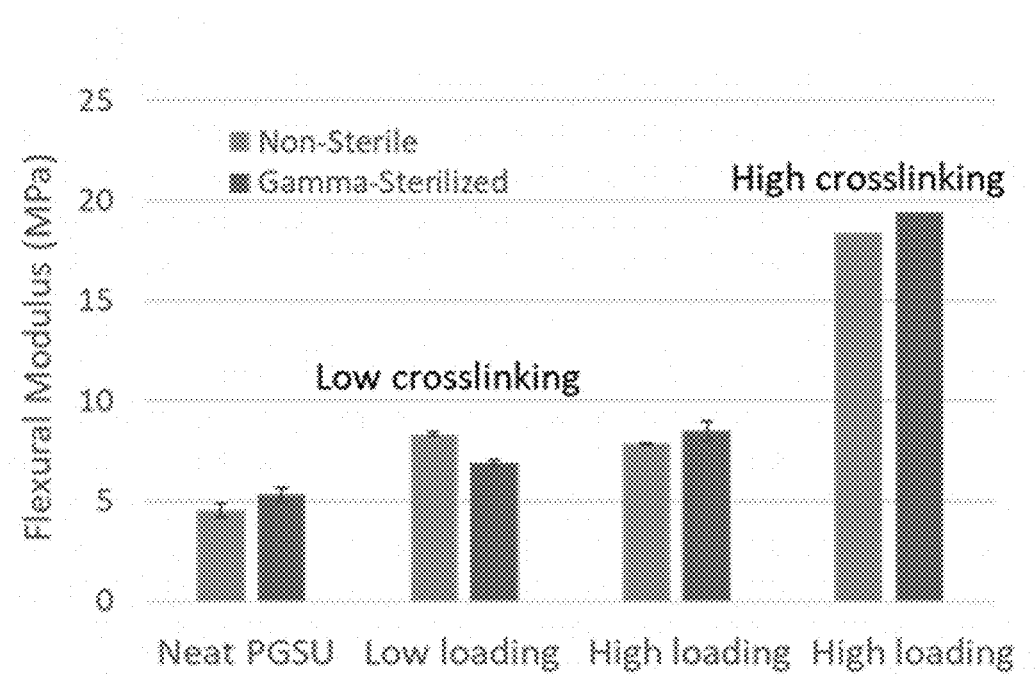
FIG. 26 shows the mechanical testing results from 3-point bending of PGSU rod products with and without 10% to 30% w/w API loading, for PGSU made from Regenerez® PGS resin.
Figure 27:
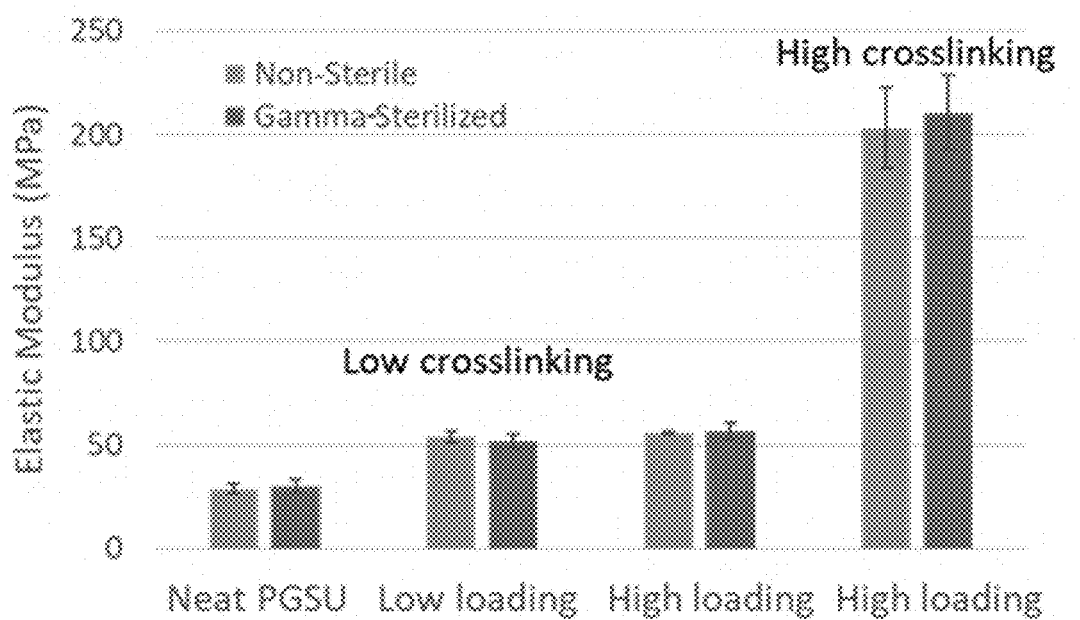
FIG. 27 shows the mechanical testing results from axial compression applied to PGSU rod products with and without 10% to 30% w/w API loading, for PGSU made from Regenerez® PGS resin.
Figure 28:
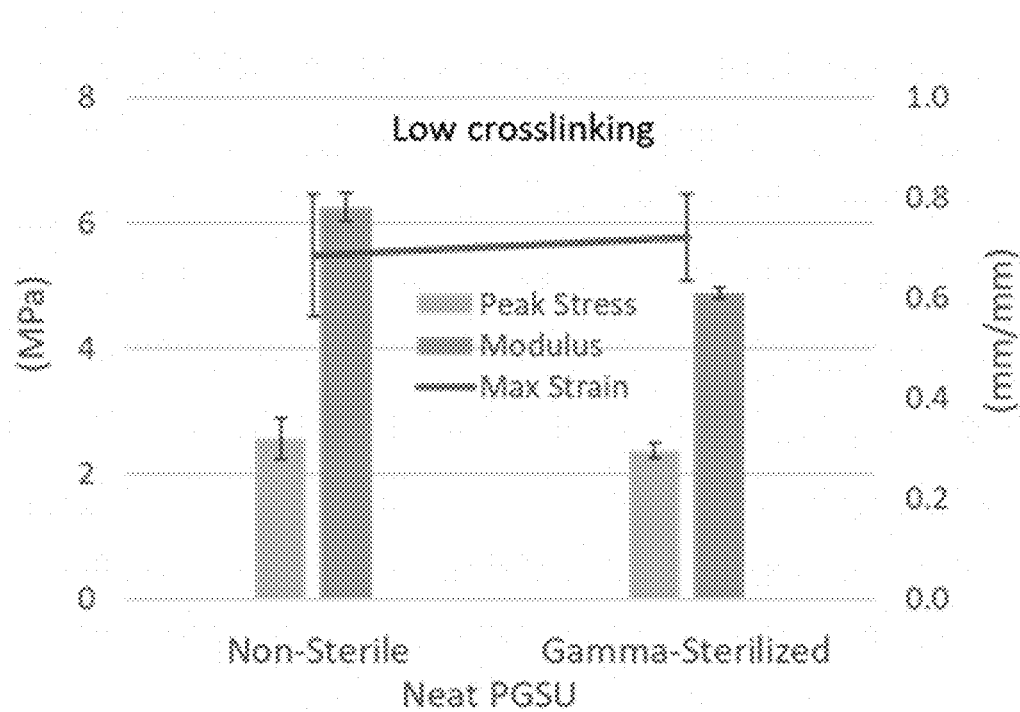
FIG. 28 shows the mechanical testing results from axial tension applied to PGSU sheets without API loading, for PGSU made from Regenerez® PGS resin.

Neat (unloaded) PGSU and (loaded) PGSU with caffeine-loading, from the same batch of rod samples referenced in Example 8, were mechanically tested before and after gamma irradiation using 3-point bending and axial compression, as shown in FIG. 26 and FIG. 27, respectively, and differences between high crosslinking and low crosslinking were observed. Unloaded PGSU sheets with a 3.6:1 PGS:HDI mass ratio were mechanically tested using axial tension, as shown in FIG. 28. No significant differences were detected between unsterilized and gamma-irradiated sterile PGSU, either for rods or sheets.

For a PGS resin with a hydroxyl number between 160 and 240, a PGS:HDI mass ratio of 3.6:1 results in an isocyanate-to-hydroxyl stoichiometric ratio between 1:0.86 and 1:1.3.

Example 16

Solvent-less PGSU rod implants were created using a high shear mixing technique followed by a dual-barrel syringe extrusion technique, formulated with 40% w/w and 60% w/w caffeine and 2:1 PGS:HDI mass ratio. Temperatures were maintained below 40° C. throughout the process.

FIG. 29A and FIG. 29B illustrate via SEM uniform caffeine distribution through the cross-section of PGSU rods formed using the solvent-less method at less than 40° C. FIG. 29A shows 40% w/w caffeine-loaded PGSU and FIG. 29B shows 60% w/w caffeine-loaded PGSU.

FIG. 30 and FIG. 31 illustrate the uniformity of rods created across a batch using the dual-barrel syringe method, demonstrating successful mixing was achieved, even at high crosslinking and high loading where large amounts of HDI and API required homogeneous incorporation. Uniformity across the batch was assessed according to crosslink density, caffeine content, and elastic modulus. FIG. 30 shows 40% w/w caffeine-loaded PGSU, and FIG. 31 is 60% w/w caffeine-loaded PGSU. Crosslinking and % caffeine were determined using a thermogravimetric analysis (TGA) method quantifying the mass loss associated with urethane crosslink content and caffeine content, respectively, and are displayed on the left-hand y-axis. Elastic modulus was determined using axial compression and is displayed on the right-hand y-axis.

For a PGS resin with a hydroxyl number between 160 and 240, a PGS:HDI mass ratio of 2:1 results in an isocyanate-to-hydroxyl stoichiometric ratio between 1:0.48 and 1:0.72.

All references cited herein are hereby incorporated by reference in their entirety.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising poly(glycerol sebacate) urethane, wherein the poly(glycerol sebacate) urethane is formed from a poly(glycerol sebacate) resin reacted with an isocyanate at an isocyanate-to-hydroxyl stoichiometric ratio in the range of 1:0.25 to 1:1.25.

2. The composition of claim 1, wherein the poly(glycerol sebacate) resin has a molecular weight greater than 10,000 Da.

3. The composition of claim 1, wherein the poly(glycerol sebacate) resin has a polydispersity index less than 12.

4. The composition of claim 1, wherein the poly(glycerol sebacate) resin has a glycerol-to-sebacic acid stoichiometric ratio of between 1:0.5 and 1:1.5.

5. The composition of claim 1, wherein the isocyanate is a blocked isocyanate.

6. The composition of claim 1, wherein the composition is free of a solvent.

7. The composition of claim 1 further comprising an active pharmaceutical ingredient mixed with the poly(glycerol sebacate) urethane, wherein the active pharmaceutical ingredient is at least 10% w/w of the composition.

8. The composition of claim 1, wherein the isocyanate-to-hydroxyl stoichiometric ratio is in the range of 1:0.25 to 1:1.

9. The composition of claim 1 further comprising at least one additive mixed with the poly(glycerol sebacate) urethane, wherein the at least one additive is at least 10% w/w of the composition and the at least one additive is selected from the group consisting of an active pharmaceutical ingredient, a filler, and a combination thereof.

10. A composition comprising poly(glycerol sebacate) urethane, wherein the poly(glycerol sebacate) urethane is formed from a poly(glycerol sebacate) resin having a polydispersity index in the range of 8 to less than 12.

11. The composition of claim 10, wherein the poly(glycerol sebacate) resin has a molecular weight greater than 10,000 Da.

12. The composition of claim 10, wherein the poly(glycerol sebacate) resin has a glycerol-to-sebacic acid stoichiometric ratio of between 1:0.5 and 1:1.5.

13. The composition of claim 10, wherein the isocyanate is a blocked isocyanate.

14. The composition of claim 10, wherein the composition is free of a solvent.

15. The composition of claim 10, wherein the isocyanate-to-hydroxyl stoichiometric ratio is in the range of 1:0.25 to 1:1.25.

16. The composition of claim 10 further comprising an active pharmaceutical ingredient mixed with the poly(glycerol sebacate) urethane, wherein the active pharmaceutical ingredient is at least 10% w/w of the composition.

17. A process of forming a poly(glycerol sebacate) urethane, the process comprising:
homogeneously mixing a flowable poly(glycerol sebacate) resin with a catalyst and a solvent to form a resin blend;
selecting an amount of isocyanate such that an isocyanate-to-hydroxyl stoichiometric ratio is in the range of 1:0.25 to 1:1.25;
homogeneously combining the resin blend with a composition comprising the isocyanate to form a reaction mixture; and
dispensing the reaction mixture to form the poly(glycerol sebacate) urethane.

18. The process of claim 17, wherein the weight average molecular weight of the flowable poly(glycerol sebacate) resin is greater than 10,000 Da.

19. The process of claim 17, wherein the homogeneously combining comprises mixing in a mixing chamber, a tip, or a nozzle.

20. The process of claim 17, wherein the resin blend and the composition comprising the isocyanate are physically separated in a dual-barrel cartridge prior to the homogeneously combining.

21. The process of claim 17, wherein the dispensing comprises spraying the reaction mixture through a spray coater nozzle.

22. The process of claim 17, wherein the dispensing coats a substrate.

23. The process of claim 22, wherein the substrate is a textile.

24. The process of claim 22, wherein the dispensing comprises spraying the reaction mixture onto the substrate to spray coat the substrate.

25. The process of claim 17, wherein the dispensing comprises spraying into air to form microparticles of the poly(glycerol sebacate) urethane.

26. A composition comprising poly(glycerol sebacate) urethane and an active pharmaceutical ingredient mixed with the poly(glycerol sebacate) urethane, wherein the poly(glycerol sebacate) urethane is formed from a poly(glycerol sebacate) resin reacted with an isocyanate at an isocyanate-to-hydroxyl stoichiometric ratio in the range of 1:0.25 to 1:5 and the active pharmaceutical ingredient mixed with the poly(glycerol sebacate) urethane is at least 40% w/w of the composition.

27. The composition of claim 26, wherein the poly(glycerol sebacate) resin has a molecular weight greater than 10,000 Da.

28. The composition of claim 26, wherein the poly(glycerol sebacate) resin has a polydispersity index less than 12.

29. The composition of claim 26, wherein the poly(glycerol sebacate) resin has a glycerol-to-sebacic acid stoichiometric ratio of between 1:0.5 and 1:1.5.

30. The composition of claim 26, wherein the isocyanate is a blocked isocyanate.

31. The composition of claim 26, wherein the composition is free of a solvent.

32. A composition comprising poly(glycerol sebacate) urethane and at least one additive mixed with the poly(glycerol sebacate) urethane, wherein the poly(glycerol sebacate) urethane is formed from a poly(glycerol sebacate) resin reacted with an isocyanate at an isocyanate-to-hydroxyl stoichiometric ratio in the range of 1:0.25 to 1:5, the at least one additive is at least 40% w/w of the composition, and the at least one additive is selected from the group consisting of an active pharmaceutical ingredient, a filler, and a combination thereof.

\* \* \* \* \*